US012790391B2

(12) United States Patent
Mitnacht-Kraus et al.

(10) Patent No.: US 12,790,391 B2
(45) **Date of Patent: *Nov. 10, 2026**

(54) ANTIBODIES USEFUL IN CANCER DIAGNOSIS

(71) Applicants: Astellas Pharma Inc., Tokyo (JP); TRON—Translationale Onkologie an der Universitätsmedizin der Johannes Gutenberg-Universität Mainz gemeinnützige GmbH, Mainz (DE)

(72) Inventors: Rita Mitnacht-Kraus, Friedberg (DE); Stefan Wöll, Stadecken-Elsheim (DE); Korden Walter, Saulheim (DE); Özlem Türeci, Mainz (DE); Ugur Sahin, Mainz (DE)

(73) Assignees: Astellas Pharma Inc., Tokyo (JP); TRON—Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 461 days.

This patent is subject to a terminal disclaimer.

(21) Appl. No.: 18/423,761

(22) Filed: Jan. 26, 2024

(65) Prior Publication Data

US 2024/0209079 A1 Jun. 27, 2024

Related U.S. Application Data

(63) Continuation of application No. 17/666,122, filed on Feb. 7, 2022, now Pat. No. 11,919,951, which is a (Continued)

(30) Foreign Application Priority Data

Sep. 6, 2017 (WO) ................ PCT/EP2017/072386

(51) Int. Cl.
*C07K 16/28* (2006.01)
*A61K 47/68* (2017.01)
(Continued)

(52) U.S. Cl.
CPC .......... *C07K 16/28* (2013.01); *A61K 47/6849* (2017.08); *G01N 33/5759* (2026.01); (Continued)

(58) Field of Classification Search
None
See application file for complete search history.

(56) References Cited

U.S. PATENT DOCUMENTS

2011/0059469 A1 3/2011 Aburatani et al.
2016/0159901 A1 6/2016 Sahin et al.

FOREIGN PATENT DOCUMENTS

EP 2070548 A1 6/2009
WO 2008013948 A2 1/2008
(Continued)

OTHER PUBLICATIONS

Anonymous: "Claudin-6 Antibody (A-4): sc-393671", Santa Cruz Biotechnology, XP002779792, Retrieved from the Internet: URL: https://www.scbt.com/scbt/product/claudin-6-antibody-a-4 [retrieved on Apr. 4, 2018] First page.
(Continued)

*Primary Examiner* — Aurora M Fontainhas
(74) *Attorney, Agent, or Firm* — Neal, Gerber & Eisenberg LLP

(57) ABSTRACT

The invention relates to antibodies directed against an epitope located within the C-terminal portion of CLDN6 which are useful, for example, in diagnosing cancer and/or in determining whether cancer cells express CLDN6.

18 Claims, 12 Drawing Sheets

Specification includes a Sequence Listing.

Related U.S. Application Data continuation of application No. 16/641,160, filed as application No. PCT/EP2018/073883 on Sep. 5, 2018, now Pat. No. 11,279,757.

(51) Int. Cl.

| | |
|---|---|
| ***C12N 5/09*** | (2010.01) |
| ***G01N 33/50*** | (2006.01) |
| ***G01N 33/575*** | (2026.01) |

(52) U.S. Cl.

CPC ...... *C07K 2317/21* (2013.01); *C07K 2317/24* (2013.01); *C07K 2317/31* (2013.01); *C07K 2317/34* (2013.01)

(56) References Cited

FOREIGN PATENT DOCUMENTS

| | | | |
|---|---|---|---|
| WO | 2009028663 | A1 | 3/2009 |
| WO | 2011057788 | A1 | 5/2011 |
| WO | 2012003956 | A1 | 1/2012 |
| WO | 2012156018 | A1 | 11/2012 |
| WO | 2015014870 | A1 | 2/2015 |
| WO | 2017187186 | A1 | 11/2017 |
| WO | 2019048489 | A1 | 3/2019 |

OTHER PUBLICATIONS

Arabzadeth et al., BMC Cancer, 7(1), 196, 1-8 (2007).
European Patent Office, International Search Report in International Application No. PCT/EP2018/073883 (Oct. 11, 2018).
European Patent Office, Written Opinion in International Application No. PCT/EP2018/073883 (Oct. 11, 2018).
Genbank, "anti-HIV-1 p24 antibody D2 kappa light chain, partial [Mus musculus]", Accession No. AAC35165.1, Jul. 25, 2016.
Genbank, "immunoglobulin heavy chain variable region, partial [Mus musculus]", Accession No. AML31993.1, Mar. 10, 2016.
Hopcraft et al. "Selection of a Hepatitis C Virus With Altered Entry Factor Requirements Reveals a Genetic Interaction Between the E1 Glycoprotein and Claudins". Hepatology. 62(4), 2015, 1059-1069.
Liu et al. "Expressions of tight junctions protein CLDN6 in ovarian cancer, liver cancer and meningioma tissues and significances". Journal of Jilin Univ. (Medicine Edition). 36(4), 2010, 698-702.
Morita et al., The Journal of Cell Biology, 147(1): 185-194 (1999).
Singer M. and Berg P., Genes & Genomes, p. 63-64 (1998).
Yarilin AA, Osnovy Immunologii [Fundamentals of Immunology], p. 171-173 (1999).
U.S. Appl. No. 16/641,160, filed Feb. 21, 2020, Patented.
U.S. Appl. No. 17/666,122, filed Feb. 7, 2022, Pending.
Dotti et al., "Design and Development of Therapies using Chimeric Antigen Receptor-Expressing T cells", Immunol Rev 257: 107-126, 2014.
Rudikoff et al., "Single amino acid substitution altering antigen-binding specificity", Proc Natl Acad Sei USA. vol 79, p. 1979, 1982.
Zhang et al., "Comprehensive optimization of a single-chain variable domain antibody fragment as a targeting ligand for a cytotoxic nanoparticle", mAbs 7(1): 42-52, 2015.
Vasudevan et al., "A single amino acid change in the binding pocket alters specificity of an anti-integrin antibody AP7.4 as revealed by its crystal structure", Blood Cell Mol Dis 32: 176-181, 2004.
Brummell et al., "Probing the Combining Site of an Anti-Carbohydrate Antibody by Saturation-Mutagenesis: Role of the Heavy-Chain CDR3 Residues", Biochemistry 32: 1180-1187, 1993.
Kobayashi et al., "Tryptophan H33 plays an important role in pyrimidine (6-4) pyrimidone photoproduct binding by a high-affinity antibody", Protein Engineering 12: 879-844, 1999.
Burks et al., "In vitro scanning saturation mutagenesis of an antibody binding pocket", PNAS 94: 412-417, 1997.
Jang et al., "The structural basis for DNA binding by an anti-DNA autoantibody", Mol Immunol 35: 1207-1217, 1998.
Brorson et al., "Mutational Analysis of Avidity and Fine Specificity of Anti-Levan Antibodies", J Immunol163: 6694-6701, 1999.
Colman, "Effects of amino acid sequence changes on antibody-antigen interactions", Res Immunol145: 33-36, 1994.
Wang, et al., "Antibody Structure, Instability, and Formulation", Journal of Pharmaceutical SCIE, American Pharmaceutical Association, Washington, US, vol. 96, No. 1, Jan. 1, 2007 pp. 1-26.
Gokarn et al., "Self-Buffering Antibody Formulations", Journal of Pharmaceutical Sciences, American Pharmaceutical Association, Washington, US, vol. 97, No. 8, Aug. 1, 2008, pp. 3051-3066.

Figure 1A

```
hsCLDN6    MASAGMQILGVVLTLLGWVNGLVSCALPMWKVTAFIGNSIVVAQVVWEGLWMSCVVQSTG
MmCLDN6    MASTGLQILGIVLTLLGWVNALVSCALPMWKVTAFIGNSIVVAQMVWEGLWMSCVVQSTG
hsCLDN9    MASTGLELLGMTLAVLGWLGTLVSCALPLWKVTAFIGNSIVVAQVVWEGLWMSCVVQSTG
           ***;*:::**:.*::***:.  *******:***************:***************

hsCLDN6    QMQCKVYDSLLALPQDLQAARALCVIALLVALFGLLVYLAGAKCTTCVEEKDSKARLVLT
MmCLDN6    QMQCKVYDSLLALPQDLQAARALCVVTLLIVLLGLLVYLAGAKCTTCVEDRNSKSRLVLI
hsCLDN9    QMQCKVYDSLLALPQDLQAARALCVIALLLALLGLLVAITGAQCTTCVEDEGAKARIVLT
           *************************;:**:.*:****  ::**;******:..:*:*;**

hsCLDN6    SGIVFVISGVLTLIPVCWTAHAIIRDFYNPLVAEAQKRELGASLYLGWAASGLLLLGGGL
MmCLDN6    SGIIFVISGVLTLIPVCWTAHSIIQDFYNPLVADAQKRELGASLYLGWAASGLLLLGGGL
hsCLDN9    AGVILLLAGILVLIPVCWTAHAIIQDFYNPLVAEALKRELGASLYLGWAAAALLMLGGGL
           :*:::::*:*.*********:**:********:* ***************:.**:*****

hsCLDN6    LCCTCPSGGSQGPSHYMARYSTSAPAISRGPSEYPTKNYV (SEQ ID NO: 1)
MmCLDN6    LCCACSSGGTQGPRHYMACYSTSVPHS-RGPSEYPTKNYV (SEQ ID NO: 5)
hsCLDN9    LCCTCPPPQVERPRGPRLGYSIPSRSGASGLDKRDYV--- (SEQ ID NO: 2)
           ***;*..     : *         ** .         * .:
```

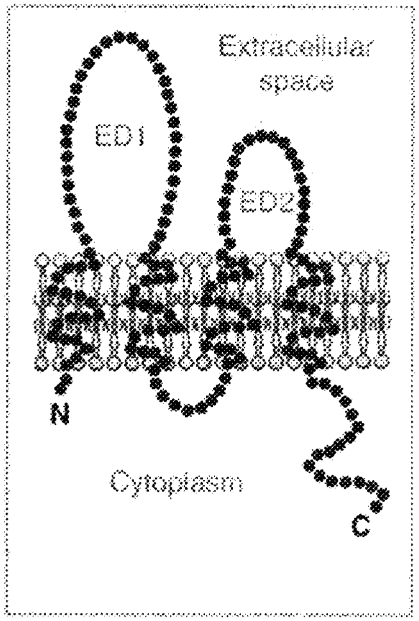

<u>Underlined</u> – Transmembrane domains according to Günzel et. al., Physiol Rev 93:525-569, 2013

Figure 1B

```
hCLDN6   ------------------------------------MASAGMQILGVVLTL 15
hCLDN9   ------------------------------------MASTGLELLGMTLAV 15
hCLDN3   -------------------------------------MSMGLEITGTALAV 14
hCLDN4   ------------------------------------MASMGLQVMGIALAV 15
                                              *  .::: *  .* :

hCLDN6   LGWVNGLVSCALPMWKVTAFIGNSIVVAQVVWEGLWMSCVVQSTGQMQCK 65
hCLDN9   LGWLGTLVSCALPLWKVTAFIGNSIVVAQVVWEGLWMSCVVQSTGQMQCK 65
hCLDN3   LGWLGTIVCCALPMWRVSAFIGSNIITSQNIWEGLWMNCVVQSTGQMQCK 64
hCLDN4   LGWLAVMLCCALPMWRVTAFIGSNIVTSQTIWEGLWMNCVVQSTGQMQCK 65
         :**    ::.*.**:*:*:**:.  .*:.:*   *:****.*******:****

hCLDN6   VYDSLLALPQDLQAARALCVIALLVALFGLLVYLAGAKCTTCVEEKDSKA 115
hCLDN9   VYDSLLALPQDLQAARALCVIALLLALLGLLVAITGAQCTTCVEDEGAKA 115
hCLDN3   VYDSLLALPQDLQAARALTVVAILLAAFGLLVALVGAQCTNCVQDDTAKA 114
hCLDN4   VYDSLLALPQDLQAARALVIISIIVAALGVLLSVVGGKCTNCLEDESAKA 115
         ****:***. ::****** : ::::* ..::: :.*.:**:*:     :**

hCLDN6   RLVLTSGIVFVISGVLTLIPVCWTAHAIIRDFYNPLVAEAQKRELGASLY 165
hCLDN9   RIVLTAGVILLLLAGILVLIPVCWTAHAIIQDFYNPLVAEALKRELGASLY 165
hCLDN3   KITIVAGVLFLLAALLTLVPVSWSANTIIRDFYNPVVPEAQKREMGAGLY 164
hCLDN4   KTMIVAGVVFLLAGLMVIVPVSWTAHNIIQDFYNPLVASGQKREMGASLY 165
         :  :..*:: ::..::.::*:.* *: ::::**:* *.  . * *:**.**

hCLDN6   LGWAASGLLLLGGGLLCCTCPSGGSQGPSHY--MARYSTSAPAISRGPSE 213
hCLDN9   LGWAAAALLMLGGGLLCCTCPPPQVERPRG----PRLGYSIPSRS-GASG 210
hCLDN3   VGWAAAALQLLGGALLCCSCPPR-EKKYTATKVVYSAPRSTGPGASLGTG 213
hCLDN4   VGWAASGLLLLGGGLLCCNCPPRTDKPYSAK---YSAARSAAASN----- 207
         :****:.:* ::** ****  .     .                .

hCLDN6   YPTKNYV 220 (SEQ ID NO: 1)
hCLDN9   LDKRDYV 217 (SEQ ID NO: 2)
hCLDN3   YDRKDYV 220 (SEQ ID NO: 3)
hCLDN4   -----YV 209 (SEQ ID NO: 4)
```

TM-domäne

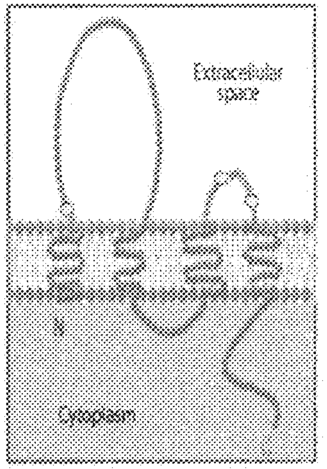

○ 3 amino acid differences between CLDN6 & CLDN9

Simplification of Claudin structure

| | 11-10A 67-3A 67-5B | 12-12A 68-30B | 37-4A 68-4A | 11-13A 12-1A 12-9A 12-14A 25-3A 25-4A 68-12A 68-34A | 25-2A 43-1A 59-1A | 22-20A | 46-2A 52-1A 64-1A | 46-5A 58-1B 58-3A 58-4B 58-4B-2 68-8B | rb-ser (IBL) |
|---|---|---|---|---|---|---|---|---|---|
| pep1 | X | X | X | | | | | | |
| pep2 | X | X | X | X | X | | | | |
| pep3 | X | X | | X | | ✓ | | | |
| pep4 | X | | | | | | | | |
| pep5 | X | | | | | | | | |
| pep6 | | | | | | | | | X |
| pep7 | | | | | | | | X | X |

X binding of mAB to peptide

Figure 4B

| | 182 … 220 | |
|---|---|---|
| **huCLDN6 C-term** | **--CTCPSGGSQGPSHYMARYSTSAPAISRGPSEYPTKNYV** (SEQ ID NO: 8) | |
| Peptid 1 | --CTCPSGGSQGPSHY------------------------ (SEQ ID NO: 9) | **Unconj. Peptide (4aa shift each peptide)** |
| Peptid 2 | --------PSGGSQGPSHYMARY---------------- (SEQ ID NO: 10) | |
| Peptid 3 | ----------------SQGPSHYMARYSTSA---------- (SEQ ID NO: 11) | |
| **Peptid 4** | **-------------------------SHYMARYSTSAPAIS-------------** (SEQ ID NO: 12) | |
| Peptid 5 | ---------------------------------ARYSTSAPAISRGPS-------- (SEQ ID NO: 13) | |
| Peptid 6 | -----------------------------------------TSAPAISRGPSEYPT---- (SEQ ID NO: 14) | |
| Peptid 7 | -------------------------------------------------AISRGPSEYPTKNYV (SEQ ID NO: 15) | |

| peptide | Biotinylated Peptides (1aa shift each peptide) | SEQ ID NO | 46-5A | 58-1B | 58-3A | 58-4B 58-4B-2 | rb-anti-CLDN6 IBL |
|---|---|---|---|---|---|---|---|
| pep4 | SHYMARYSTSAPAIS | 12 | | | | | |
| pep4A | YMARYSTSAPAISRG | 16 | | | | | |
| pep11 | ARYSTSAPAISRGPS | 13 | | | | | X |
| pep12 | RYSTSAPAISRGPSE | 17 | | | | | X |
| pep13 | YSTSAPAISRGPSEY | 18 | | | | | X |
| pep14 | STSAPAISRGPSEYP | 19 | | | | | X |
| pep15 | TSAPAISRGPSEYPT | 14 | | | | | X |
| pep16 | SAPAISRGPSEYPTK | 20 | X | | | | X |
| pep17 | APAISRGPSEYPTKN | 21 | X | | | | X |
| pep18 | PAISRGPSEYPTKNY | 22 | X | X | X | X | X |
| pep19 | AISRGPSEYPTKNYV | 15 | X | X | X | X | X |
| pep20 | ISRGPSEYPTKNYV | 23 | X | X | X | X | X |
| pep21 | SRGPSEYPTKNYV | 24 | X | X | X | X | X |
| pep22 | RGPSEYPTKNYV | 25 | X | X | X | X | X |
| pep23 | GPSEYPTKNYV | 26 | X | X | X | X | <50% |
| pep24 | PSEYPTKNYV | 27 | X | X | X | X | <50% |
| pep25 | SEYPTKNYV | 28 | X | X | X | X | |
| pep26 | EYPTKNYV | 29 | X | X | X | X | |
| pep27 | YPTKNYV | 30 | | | | | |
| pep28 | PTKNYV | 31 | | | | | |
| pep29 | PTKNY | 32 | | | | | |
| pep30 | PTKN | 33 | | | | | |

CLDN6 C-term Sequence
aa181
220
hsCLDN6 LCCTCPSGGSQGPSHY--MARYSTSAPAISRGPSEYPTKNYV (SEQ ID NO: 34)
hsCLDN9 LCCTCPPPQVERPRG----PRLGYSIPSRS-GASGLDKRDYV (SEQ ID NO: 35)
hsCLDN3 LCCSCPPR-EKKYTATKVVYSAPRSTGPGASLGTGYDRKDYV (SEQ ID NO: 36)
hsCLDN4 LCCNCPPRTDKPYSAK---YSAARSAAASN---------YV (SEQ ID NO: 37)
IBL
58-4B-2

Figure 5A 58-4B variable *kappa* chain (SEQ ID NO: 41)

---FR1--- ---CDR1--- ---FR2--- CDR2 ---FR3--- ---CDR3--- ---FR4---

DIVLTQNPLTLSVTIGQTASISCKSS QNLLYSDGKTY LNWLLQRPGQSPKRLIY LMS KLDSGVPDRFTGSGSGTDFTLKISRVEAEDLGVYYC WQGTHFPWT FGGGTKLENT 58-4B variable heavy chain (SEQ ID NO: 40)

---FR1--- --CDR1--- ---FR2--- --CDR2-- ---FR3--- --CDR3- ---FR4---

EVQLQQSGTVLARPGASVRMSCRTS GYIFTTYW IHWVKERPGQGLVWIGA IFPGNSDT TYNQKFRGKASLTAVTSASTAYLDLSSLTDEDSAVYYC TREFYAT WGQGTTLTVSS 58-1B variable *kappa* chain (SEQ ID NO: 43)

---FR1--- ---CDR1--- ---FR2--- CDR2 ---FR3--- ---CDR3--- ---FR4---

DVVMTQNPLTLSVTIGQTASISCKSS QNLLYSDGKTY LNWLLQRPGQSPKRLIY LMS KLDSGVPDRFTGSGSRTDFTLKISRVEAEDLGVYYC WQGTHFPWT FGGGTKLEIT 58-1B variable heavy chain (SEQ ID NO: 42)

---FR1--- ---CDR1--- ---FR2--- --CDR2--- ---FR3--- --CDR3--- ---FR4---

EVQLQQSGTVLARPGASVKMSCRTS GYTFTTYW MHWVRERPGQGLEWIGA IYPENSDA TYNQKFKGKASLTAVTSASTAYLELSSLTDEDSAVYYC TREFYAT WGQGTTLTVSS

Figure 5B 58-3A variable *kappa* chain (SEQ ID NO: 45)

---FR1--- ---CDR1--- ---FR2--- CDR2 ---FR3--- ---CDR3--- ---FR4---

DIVLTQNPLTLSVTIGQTASISCKSS QNLLYSDGKTY LNWLLQRPGQSPKRLIY LMS KLESGVPDRFTGSGSGTEFTLKISRVEAEDLGVYYC WQGTHFPWT FGGGTKLEIS 58-3A variable heavy chain (SEQ ID NO: 44)

---FR1--- --CDR1--- ---FR2--- --CDR2-- ---FR3--- --CDR3- ---FR4---

EVQLQQSGTVLARPGASVKMSCRTS GYTFTTYW MHWVRERPGQGLEWIGA IYPENSDA TYNQKFKGKASLTAVTSASTAYLELSSLTDEDSAVYYC TREFYAT WGQGTTLTVSS

Figure 7

| Applicant's or agent's file reference 342-99 PCT | International application No. |
|---|---|

INDICATIONS RELATING TO DEPOSITED MICROORGANISM OR OTHER BIOLOGICAL MATERIAL

(PCT Rule 13*bis*)

A. The indications made below relate to the deposited microorganism or other biological material referred to in the description on page 4, line 20.

B. IDENTIFICATION OF DEPOSIT — Further deposits are identified on an additional sheet [X]

Name of depositary institution
DSMZ-Deutsche Sammlung von Mikroorganismen und Zellkulturen GmbH Address of depositary institution *(including postal code and country)*
Inhoffenstr. 7 B
38124 Braunschweig
DE

| Date of deposit | Accession Number |
|---|---|
| November 29, 2016 | DSM ACC3311 |

C. ADDITIONAL INDICATIONS *(leave blank if not applicable)* — This information is continued on an additional sheet [ ]

- Mouse (Mus musculus) myeloma Ag8.653 fused with mouse (Mus musculus) splenocytes
- Hybridoma secreting antibody against human CLDN6

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July1998; reprint January 2004)

ANTIBODIES USEFUL IN CANCER DIAGNOSIS

CROSS-REFERENCE TO RELATED APPLICATIONS

This application is a continuation of U.S. patent application Ser. No. 17/666,122, which was filed on Feb. 7, 2022, which is a continuation of U.S. patent application Ser. No. 16/641,160, which was filed on Feb. 21, 2020, which is a National Stage Entry of International Application Number PCT/EP2018/073883, which was filed on Sep. 5, 2018 and claimed priority to International Application Number PCT/EP2017/072386, which was filed on Sep. 6, 2017. The contents of each of the aforementioned applications are incorporated herein by reference in their entireties.

SEQUENCE LISTING

The computer-readable Sequence Listing submitted on Jan. 26, 2024 and identified as follows: 75,409 bytes ST.26 XML document file named "026156-8054 Sequence Listing.xml," created Jan. 25, 2024, is incorporated herein by reference in its entirety.

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signaling.

Claudin-6 (CLDN6) is an oncofetal gene expressed in murine and human stem cells as well as embryoid bodies committed to the epithelia cell fate (Turksen, K. et al. (2001) Dev Dyn 222, 292-300; Anderson W J. et al. (2008) Dev Dyn 237, 504-12; Turksen K. et al. (2002) Development, 129, 1775-84; Assou S. et al. (2007) Stem Cells 25, 961-73). As a tumor-associated antigen it can be classified as a differentiation antigen due to its expression during early stage of epidermal morphogenesis where it is crucial for epidermal differentiation and barrier formation. Additionally expression was observed in epithelial tissues or neonatal normal epithelial tissue of tongue, skin, stomach and breast (Abuazza G. et al. (2006), Am J Physiol Renal Physiol 291, 1132-1141; Troy T. C. et al. (2007), Molecular Biotechnology 36, 166-74; Zhao L. et al. (2008), Am J Physiol Regul Integr Comp Physiol 294, 1856-1862). Besides that, own data also reveal low or very low expression of CLDN6 in human placenta, urinary bladder, endometrium, prostate and the peripheral nerve and frequent overexpression of CLDN6 in different cancers. CLDN6 has been demonstrated to be overexpressed in tumors, including pediatric brain tumors, gastric adenocarcinomas and germ cell tumors as well as visceral carcinomas such as ovarian carcinomas. It has also been demonstrated that overexpression of CLDN6 in gastric cancer cells results in increased invasiveness, migration and proliferation suggesting that CLDN6 is a marker for poor prognosis and may play a potential role in maintaining the malignant phenotype. In addition, it has been shown that CLDN6 functions as cancer suppressor via inhibition of cell proliferation and induction of apoptosis in breast cancer cell lines.

The sequence alignment of CLDN3, CLDN4, CLDN6 and CLDN9 shown in FIG. 1B illustrates that there is a high degree of conservation of CLDN6 to other claudin proteins. This high homology of CLDN6 with other claudin proteins, in particular CLDN9 and CLDN4, render it difficult to provide CLDN6 antibodies which have properties such as specificity and affinity suitable for diagnostic purposes. The present inventors found that antibodies directed against a certain epitope located within the C-terminal portion of CLDN6 fulfill the criteria for the diagnostic applicability of antibodies, in particular for detecting and identifying cells expressing CLDN6.

The antibodies of the invention are useful, for example, in diagnosing cancer and/or in determining whether cancer cells express CLDN6. Preferably, a cancer disease or a cancer cell is characterized by surface expression of CLDN6. Cancer cells expressing CLDN6 are suitable targets for therapies targeting CLDN6 such as therapy with antibodies directed against CLDN6. In one embodiment, cancer cells express or aberrantly express CLDN6 while the corresponding normal cells do not express CLDN6 or express CLDN6 at a lower level.

SUMMARY OF THE INVENTION

In one aspect, the present invention relates to an antibody or antigen-binding fragment thereof, which binds:

(i) to a peptide having the amino acid sequence EYPTKNY (SEQ ID NO: 38), and/or (ii) to claudin 6 (CLDN6), wherein said antibody or antigen-binding fragment thereof binds to CLDN6 by binding at least to an epitope within CLDN6 having the amino acid sequence EYPTKNY (SEQ ID NO: 38), and/or (iii) to a peptide having the amino acid sequence EYPTKNYV (SEQ ID NO: 29), and/or (iv) to claudin 6 (CLDN6), wherein said antibody or antigen-binding fragment thereof binds to CLDN6 by binding at least to an epitope within CLDN6 having the amino acid sequence EYPTKNYV (SEQ ID NO: 29), and/or (v) to a peptide having the amino acid sequence AISRGPSEYPTKNYV (SEQ ID NO: 15), wherein the antibody or antigen-binding fragment thereof does not bind to a peptide having the amino acid sequence TSAPAISRGPSEYPT (SEQ ID NO: 14), and/or (vi) to claudin 6 (CLDN6), wherein said antibody or antigen-binding fragment thereof binds to CLDN6 by binding at least to an epitope within CLDN6 having the amino acid sequence AISRGPSEYPTKNYV (SEQ ID NO: 15), wherein the antibody or antigen-binding fragment thereof does not bind to a peptide having the amino acid sequence TSAPAISRGPSEYPT (SEQ ID NO: 14).

In embodiments of aspects described herein and in further aspects, the present invention relates to a monoclonal antibody or antigen-binding fragment thereof which (i) binds to a peptide having the amino acid sequence AISRGPSEYPTKNYV (SEQ ID NO: 15) and/or (ii) binds to claudin 6 (CLDN6), wherein said antibody or antigen-binding fragment thereof binds to CLDN6 by binding at least to an epitope within CLDN6 having the amino acid sequence AISRGPSEYPTKNYV (SEQ ID NO: 15).

In embodiments of aspects described herein and in further aspects, the present invention relates to an antibody or antigen-binding fragment thereof, which binds to one or more, preferably all, of the following peptides:

PAISRGPSEYPTKNY (SEQ ID NO: 22), AISRGPSEYPTKNYV (SEQ ID NO: 15), ISRGPSEYPTKNYV (SEQ ID NO: 23), SRGPSEYPTKNYV (SEQ ID NO: 24), RGP-

SEYPTKNYV (SEQ ID NO: 25), GPSEYPTKNYV (SEQ ID NO: 26), PSEYPTKNYV (SEQ ID NO: 27), SEYPTKNYV (SEQ ID NO: 28), and EYPTKNYV (SEQ ID NO: 29), wherein the antibody or antigen-binding fragment thereof does not bind to a peptide having the amino acid sequence TSAPAISRGPSEYPT (SEQ ID NO: 14).

In one embodiment, the difference in binding affinity to the peptide to which the antibody or antigen binding fragment binds with the lowest affinity and to the peptide to which the antibody or antigen binding fragment binds with the highest affinity is 50% or less, 40% or less, 30% or less, 20% or less, or 10% or less.

Antibodies or antigen-binding fragments described herein preferably do not bind to a peptide comprising the amino acid sequence EYPTK (SEQ ID NO: 59) and/or the amino acid sequence EYPTKN (SEQ ID NO: 60) but not comprising the amino acid sequence EYPTKNY (SEQ ID NO: 38). In other words, an antibody or antigen-binding fragment described herein which binds to a peptide having the amino acid sequence EYPTKNY (SEQ ID NO: 38) and/or a peptide having the amino acid sequence EYPTKNYV (SEQ ID NO: 29) binds to said peptide(s) due to the presence of the second tyrosine which is missing in the amino acid sequence EYPTK (SEQ ID NO: 59) and/or the amino acid sequence EYPTKN (SEQ ID NO: 60). As shown herein, preferred antibodies or antigen-binding fragments do not bind to a peptide comprising the amino acid sequence YPTKNY (SEQ ID NO: 61) and/or EYPTKN (SEQ ID NO: 60) but not comprising the amino acid sequence EYPTKNY (SEQ ID NO: 38) suggesting that the amino acid sequence EYPTKNY (SEQ ID NO: 38) is a sequence that can be considered to be a minimal epitope for binding of these antibodies.

In embodiments of aspects described herein and in further aspects, the present invention relates to an antibody produced by or obtainable from a hybridoma deposited at the DSMZ (Inhoffenstr. 7B, 38124 Braunschweig, Germany) and having one of the following designations and accession numbers:

1. 58-4B-2, accession no. DSM ACC3311, deposited on Nov. 29, 2016;
2. 58-3A, accession no. DSM ACC3312, deposited on Nov. 29, 2016; or
3. 58-1B, accession no. DSM ACC3313, deposited on Nov. 29, 2016.

Antibodies of the invention are designated herein by referring to the designation of the antibody and/or by referring to the clone producing the antibody.

The present invention also relates to an antibody which competes for CLDN6 binding with an antibody produced by and obtainable from the above-described hybridomas and/or has the specificity for CLDN6 of an antibody produced by or obtainable from the above-described hybridomas. In these and other embodiment, the present invention also relates to an antibody comprising an antigen binding portion or antigen binding site, in particular a variable region, identical or highly homologous to that of the antibodies produced by or obtainable from the above-described hybridomas. It is contemplated that preferred antibodies are those having CDR regions either identical or highly homologous to the CDR regions of antibodies produced by or obtainable from the above-described hybridomas. By "highly homologous" it is contemplated that from 1 to 5, preferably from 1 to 4, such as 1 to 3 or 1 or 2 substitutions may be made in each CDR region. Particularly preferred antibodies are the chimerized and humanized forms of the antibodies produced by or obtainable from the above-described hybridomas.

Accordingly, in embodiments of aspects described herein and in further aspects, the present invention relates to an antibody selected from the group consisting of:

(i) an antibody produced by or obtainable from a clone deposited under the accession no. DSM ACC3313 (58-1B), DSM ACC3312 (58-3A) or DSM ACC3311 (58-4B-2), (ii) an antibody which is a chimerized or humanized form of the antibody under (i), (iii) an antibody which competes for CLDN6 binding with an antibody under (i), (iv) an antibody which has the specificity of the antibody under (i), and (v) an antibody comprising the antigen binding portion or antigen binding site of the antibody under (i), or an antigen-binding fragment of the antibody under any one of (i) to (v).

In one embodiment, the antigen binding portion or antigen binding site of the antibody under (i) comprises the variable region of the antibody under (i).

In embodiments of aspects described herein and in further aspects, the present invention relates to an antibody selected from the group consisting of:

(a) an antibody comprising:

an antibody heavy chain comprising:

(i) an antibody heavy chain sequence comprising the sequence according to SEQ ID NO: 40, 42, or 44, or a variant thereof, (ii) at least one, preferably two, more preferably all three of the CDR sequences of an antibody heavy chain sequence comprising the sequence according to SEQ ID NO: 40, 42, or 44, or a variant thereof, or (iii) a CDR3 sequence according to SEQ ID NO: 53 or a variant thereof and preferably further comprising a CDR1 sequence according to SEQ ID NO: 51 or 57, or a variant thereof and/or a CDR2 sequence according to SEQ ID NO: 52 or 58, or a variant thereof, and (b) an antibody which competes for CLDN6 binding with an antibody according to (a) and/or has the specificity for CLDN6 of an antibody according to (a), or an antigen-binding fragment of said antibody.

In embodiments of aspects described herein and in further aspects, the present invention relates to an antibody selected from the group consisting of:

(a) an antibody comprising:

an antibody light chain comprising:

(i) an antibody light chain sequence comprising the sequence according to SEQ ID NO: 41, 43, or 45, or a variant thereof, (ii) at least one, preferably two, more preferably all three of the CDR sequences of an antibody light chain sequence comprising the sequence according to SEQ ID NO: 41, 43, or 45, or a variant thereof, or (iii) a CDR3 sequence according to SEQ ID NO: 56 or a variant thereof and preferably further comprising a CDR1 sequence according to SEQ ID NO: 54, or a variant thereof and/or a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In embodiments of aspects described herein and in further aspects, the present invention relates to an antibody selected from the group consisting of:

(a) an antibody comprising:

(I) an antibody heavy chain comprising:

(i) an antibody heavy chain sequence comprising the sequence according to SEQ ID NO: 40, 42, or 44, or a variant thereof, (ii) at least one, preferably two, more preferably all three of the CDR sequences of an antibody heavy chain sequence comprising the sequence according to SEQ ID NO: 40, 42, or 44, or a variant thereof, or (iii) a CDR3 sequence according to SEQ ID NO: 53 or a variant thereof and preferably further comprising a CDR1 sequence according to SEQ ID NO: 51 or 57, or a variant thereof and/or a CDR2 sequence according to SEQ ID NO: 52 or 58, or a variant thereof, and/or (II) an antibody light chain comprising:

(i) an antibody light chain sequence comprising the sequence according to SEQ ID NO: 41, 43, or 45, or a variant thereof, (ii) at least one, preferably two, more preferably all three of the CDR sequences of an antibody light chain sequence comprising the sequence according to SEQ ID NO: 41, 43, or 45, or a variant thereof, or (iii) a CDR3 sequence according to SEQ ID NO: 56 or a variant thereof and preferably further comprising a CDR1 sequence according to SEQ ID NO: 54, or a variant thereof and/or a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising:

(I) an antibody heavy chain comprising:

(i) an antibody heavy chain sequence comprising the sequence according to SEQ ID NO: 40, or a variant thereof, (ii) at least one, preferably two, more preferably all three of the CDR sequences of an antibody heavy chain sequence comprising the sequence according to SEQ ID NO: 40, or a variant thereof, or (iii) a CDR3 sequence according to SEQ ID NO: 53 or a variant thereof and preferably further comprising a CDR1 sequence according to SEQ ID NO: 51, or a variant thereof and/or a CDR2 sequence according to SEQ ID NO: 52, or a variant thereof, and (II) an antibody light chain comprising:

(i) an antibody light chain sequence comprising the sequence according to SEQ ID NO: 41, or a variant thereof, (ii) at least one, preferably two, more preferably all three of the CDR sequences of an antibody light chain sequence comprising the sequence according to SEQ ID NO: 41, or a variant thereof, or (iii) a CDR3 sequence according to SEQ ID NO: 56 or a variant thereof and preferably further comprising a CDR1 sequence according to SEQ ID NO: 54, or a variant thereof and/or a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising:

(I) an antibody heavy chain comprising:

(i) an antibody heavy chain sequence comprising the sequence according to SEQ ID NO: 42, or a variant thereof, (ii) at least one, preferably two, more preferably all three of the CDR sequences of an antibody heavy chain sequence comprising the sequence according to SEQ ID NO: 42, or a variant thereof, or (iii) a CDR3 sequence according to SEQ ID NO: 53 or a variant thereof and preferably further comprising a CDR1 sequence according to SEQ ID NO: 57, or a variant thereof and/or a CDR2 sequence according to SEQ ID NO: 58, or a variant thereof, and (II) an antibody light chain comprising:

(i) an antibody light chain sequence comprising the sequence according to SEQ ID NO: 43, or a variant thereof, (ii) at least one, preferably two, more preferably all three of the CDR sequences of an antibody light chain sequence comprising the sequence according to SEQ ID NO: 43, or a variant thereof, or (iii) a CDR3 sequence according to SEQ ID NO: 56 or a variant thereof and preferably further comprising a CDR1 sequence according to SEQ ID NO: 54, or a variant thereof and/or a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising:

(I) an antibody heavy chain comprising:

(i) an antibody heavy chain sequence comprising the sequence according to SEQ ID NO: 44, or a variant thereof, (ii) at least one, preferably two, more preferably all three of the CDR sequences of an antibody heavy chain sequence comprising the sequence according to SEQ ID NO: 44, or a variant thereof, or (iii) a CDR3 sequence according to SEQ ID NO: 53 or a variant thereof and preferably further comprising a CDR1 sequence according to SEQ ID NO: 57, or a variant thereof and/or a CDR2 sequence according to SEQ ID NO: 58, or a variant thereof, and (II) an antibody light chain comprising:

(i) an antibody light chain sequence comprising the sequence according to SEQ ID NO: 45, or a variant thereof, (ii) at least one, preferably two, more preferably all three of the CDR sequences of an antibody light chain sequence comprising the sequence according to SEQ ID NO: 45, or a variant thereof, or (iii) a CDR3 sequence according to SEQ ID NO: 56 or a variant thereof and preferably further comprising a CDR1 sequence according to SEQ ID NO: 54, or a variant thereof and/or a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising an antibody heavy chain comprising a CDR3 sequence according to SEQ ID NO: 53 or a variant thereof and an antibody light chain comprising a CDR3 sequence according to SEQ ID NO: 56 or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising an antibody heavy chain comprising a CDR3 sequence according to SEQ ID NO: 53 or a variant thereof and further comprising a CDR1 sequence according to SEQ ID NO: 51, or a variant thereof and a CDR2 sequence according to SEQ ID NO: 52, or a variant thereof, and an antibody light chain comprising a CDR3 sequence according to SEQ ID NO: 56 or a variant thereof and further comprising a CDR1 sequence according to SEQ ID NO: 54, or a variant thereof and a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising an antibody heavy chain comprising a CDR3 sequence according to SEQ ID NO: 53 or a variant thereof and further comprising a CDR1 sequence according to SEQ ID NO: 57, or a variant thereof and a CDR2 sequence according to SEQ ID NO: 58, or a variant thereof, and an antibody light chain comprising a CDR3 sequence according to SEQ ID NO: 56 or a variant thereof and further comprising a CDR1 sequence according to SEQ ID NO: 54, or a variant thereof and a CDR2 sequence according to SEQ ID NO: 55, or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising a heavy chain variable region (VH) comprising an amino acid sequence represented by SEQ ID NO: 40 or a variant thereof and a light chain variable region (VL) comprising an amino acid sequence represented by SEQ ID NO: 41 or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising a heavy chain variable region (VH) comprising an amino acid sequence represented by SEQ ID NO: 42 or a variant thereof and a light chain variable region (VL) comprising an amino acid sequence represented by SEQ ID NO: 43 or a variant thereof, and (b) an antibody which competes for CLDN6 binding with an antibody according to (a) and/or has the specificity for CLDN6 of an antibody according to (a), or an antigen-binding fragment of said antibody.

In certain preferred embodiments, the present invention relates to an antibody selected from the group consisting of:

(a) an antibody comprising a heavy chain variable region (VH) comprising an amino acid sequence represented by SEQ ID NO: 44 or a variant thereof and a light chain variable region (VL) comprising an amino acid sequence represented by SEQ ID NO: 45 or a variant thereof, and (b) an antibody which competes for CLDN6 binding with an antibody according to (a) and/or has the specificity for CLDN6 of an antibody according to (a), or an antigen-binding fragment of said antibody.

In preferred embodiments, an antibody of the invention comprises an antibody heavy chain comprising a gamma-2a heavy chain constant region, preferably a human gamma-2a heavy chain constant region and/or comprises an antibody light chain comprising a kappa light chain constant region.

The antibodies or antigen-binding fragments described herein bind to CLDN6. An antibody or antigen-binding fragment of the invention is preferably able to bind to CLDN6 in its native, i.e. naturally occurring or non-denatured state, or in its denatured state. In one embodiment, an antibody or antigen-binding fragment thereof of the invention binds to CLDN6 but not to CLDN9 and preferably does not bind to CLDN4 and/or CLDN3. Preferably, an antibody or antigen-binding fragment thereof of the invention does not substantially bind to a CLDN protein other than CLDN6. Preferably, an antibody or antigen-binding fragment thereof of the invention is specific for CLDN6.

In one embodiment, CLDN6 is cell surface membrane-bound CLDN6. In one embodiment, CLDN6 is present on cancer cells, wherein said cancer cells are preferably CLDN6 expressing cancer cells. In one embodiment, said cancer cells are cells from a cancer selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one embodiment, an antibody of the invention is a chimeric, human or humanized antibody. In one embodiment, an antibody of the invention is a monoclonal antibody.

In one embodiment, an antibody of the invention is obtainable by a method comprising the step of immunizing an animal with a peptide comprising, preferably consisting of the amino acid sequence of SEQ ID NO: 49, or an immunologically equivalent peptide, or a nucleic acid or host cell expressing said peptide. Preferably said peptide comprises not more than 110, 100, 90, 80, 70, 60, 50, or 40 contiguous amino acids of CLDN6.

Antibodies or antigen-binding fragments of the invention may be coupled, i.e. covalently or non-covalently linked, to other moieties such as detectable labels.

In a further aspect, the present invention relates to a conjugate comprising an antibody or antigen-binding fragment described herein coupled to at least one detectable label.

The present invention also relates to a cell such as a hybridoma producing an antibody as described herein.

Preferred hybridomas are those deposited at the DSMZ (Inhoffenstr. 7B, 38124 Braunschweig, Germany) and having one of the following designations and accession numbers:

1. 58-4B-2, accession no. DSM ACC3311, deposited on Nov. 29, 2016;
2. 58-3A, accession no. DSM ACC3312, deposited on Nov. 29, 2016; or
3. 58-1B, accession no. DSM ACC3313, deposited on Nov. 29, 2016.

The present invention also relates to a peptide comprising, preferably consisting of the amino acid sequence of SEQ ID NO: 49, or an immunologically equivalent peptide.

Preferably said peptide comprises not more than 110, 100, 90, 80, 70, 60, 50, or 40 contiguous amino acids of CLDN6.

The present invention also relates to nucleic acids encoding antibodies or parts thereof, e.g. an antibody chain, or antigen-binding fragments, or peptides as described herein. Preferably, a nucleic acid of the invention is operatively attached to one or more expression control elements allowing expression in eukaryotic or prokaryotic cells. Control elements ensuring expression in eukaryotic or prokaryotic cells are well known to those skilled in the art.

A nucleic acid of the invention may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Methods for construction of nucleic acid molecules, for construction of vectors comprising nucleic acid molecules, for introduction of vectors into appropriately chosen host cells, or for causing or achieving expression of nucleic acid molecules are well-known in the art.

A further aspect of the present invention relates to a host cell comprising a nucleic acid or vector as disclosed herein.

A further aspect the present invention relates to the detection of CLDN6 or CLDN6-expressing cells or determination of the quantity of CLDN6 or CLDN6-expressing cells using an antibody or antigen-binding fragment of the invention. CLDN6 or CLDN6-expressing cells are detected or the quantity of CLDN6 or CLDN6-expressing cells is determined by detecting or determining the amount of a complex between CLDN6 and an antibody or antigen-binding fragment of the invention. Formation of a complex indicates the presence of CLDN6 or CLDN6-expressing cells. Such detection or determination of the amount may be carried out in a number of ways, including but not limited to immunodetection using an antibody or antigen-binding fragment of the invention. Methods for using antibodies to detect peptides or proteins are well known and include ELISA, competitive binding assays, and the like. In general, such assays use an antibody or antibody fragment that specifically binds the target peptide or protein directly or indirectly bound to a label that provides for detection, e.g. indicator enzymes, radiolabels, fluorophores, or paramagnetic particles. The methods of the invention allow quantitative and/or qualitative evaluations, e.g., absolute and/or relative evaluations, of CLDN6 levels or of levels of CLDN6-expressing cells.

In one aspect, the present invention relates to a method for detecting CLDN6 or determining the quantity of CLDN6 in a sample comprising the steps of:

(i) contacting a sample with an antibody or antigen-binding fragment of the invention or a conjugate of the invention and
(ii) detecting the formation of a complex or determining the quantity of a complex between the antibody, the antigen-binding fragment or the conjugate and CLDN6.

In one embodiment, the sample is a cellular sample, i.e. a sample comprising cells such as cancer cells. In this embodiment, the complex is preferably formed between the antibody, the antigen-binding fragment or the conjugate and CLDN6 expressed by cells in said sample.

In one aspect, the present invention relates to a method for determining whether cells express CLDN6 comprising the steps of:

(i) contacting a cellular sample with an antibody or antigen-binding fragment of the invention or a conjugate of the invention and
(ii) detecting the formation of a complex between the antibody, the antigen-binding fragment or the conjugate and CLDN6 expressed by cells in said sample.

In one embodiment, the cells in the sample are cancer cells. The complex is preferably formed between the antibody, the antigen-binding fragment or the conjugate and CLDN6 expressed by cells in said sample.

Further aspects of the present invention relate to methods of diagnosing or classifying diseases by targeting CLDN6 using an antibody or antigen-binding fragment of the invention. These methods provide for the selective detection of cells that express CLDN6 thereby differentiating these cells from normal cells not expressing CLDN6 or diseased cells not expressing CLDN6. Diseases characterized by diseased cells expressing CLDN6 are treatable by a therapy targeting CLDN6 such as therapy with therapeutic antibodies directed against CLDN6. Preferred diseases for a therapy or diagnosis are those in which CLDN6 is expressed or aberrantly expressed, in particular cancer diseases, such as those described herein.

In one aspect the present invention relates to methods for diagnosis, detection or monitoring, i.e. determining the regression, progression, course and/or onset, of a cancer disease comprising the detection of CLDN6 or CLDN6-expressing cells and/or determination of the quantity of CLDN6 or CLDN6-expressing cells in a biological sample isolated from a patient using an antibody or antigen-binding fragment of the invention. Such methods may be used to detect whether a subject has a cancer disease or is at (increased) risk of developing a cancer disease or, for instance, whether a treatment regimen is efficient.

Thus, in one aspect, the present invention relates to a method for diagnosis, detection or monitoring of cancer comprising the steps of:

(i) contacting a biological sample with an antibody or antigen-binding fragment of the invention or a conjugate of the invention and (ii) detecting the formation of a complex and/or determining the quantity of a complex between the antibody, the antigen-binding fragment or the conjugate and CLDN6.

In one embodiment, the biological sample is a cellular sample, i.e. a sample comprising cells such as cancer cells. In this embodiment, the complex is preferably formed between the antibody, the antigen-binding fragment or the conjugate and CLDN6 expressed by cells in said sample.

The methods of monitoring according to the invention preferably comprise a detection of and/or determination of the quantity of CLDN6 or CLDN6-expressing cells in a first sample at a first point in time and in a further sample at a second point in time, wherein the regression, progression, course and/or onset of a tumor disease may be determined by comparing the two samples.

Typically, the level of CLDN6 or level of CLDN6-expressing cells in a biological sample is compared to a reference level, wherein a deviation from said reference level is indicative of the presence and/or stage of a cancer disease in a subject. The reference level may be a level as determined in a control sample (e.g., from a healthy tissue or subject, in particular a patient without a cancer disease) or a median level from healthy subjects. A "deviation" from said reference level designates any significant change, such as an increase by at least 10%, 20%, or 30%, preferably by at least 40% or 50%, or even more.

Preferably, the presence of CLDN6 or CLDN6-expressing cells and/or a quantity of CLDN6 or CLDN6-expressing cells which is increased compared to a reference level, e.g. compared to a patient without a cancer disease, indicates the presence of or risk for (i.e. a potential for a development of) a cancer disease in the patient.

A quantity of CLDN6 or CLDN6-expressing cells which is decreased compared to a biological sample taken earlier from a patient may indicate a regression, a positive course, e.g. a successful treatment, or a reduced risk for an onset of a cancer disease in a patient.

A quantity of CLDN6 or CLDN6-expressing cells which is increased compared to a biological sample taken earlier from a patient may indicate a progression, a negative course, e.g. an unsuccessful treatment, recurrence or metastatic behavior, an onset or a risk for an onset of a cancer disease in said patient.

In one aspect, the present invention relates to a method for determining whether a cancer is treatable by a cancer therapy targeting CLDN6 comprising the steps of:

(i) contacting a sample comprising cancer cells with an antibody or antigen-binding fragment of the invention or a conjugate of the invention and (ii) detecting the formation of a complex between the antibody, the antigen-binding fragment or the conjugate and CLDN6.

The complex is preferably formed between the antibody, the antigen-binding fragment or the conjugate and CLDN6 expressed by cancer cells in said sample.

Such methods may be used to detect whether a patient is suitable for a therapy involving the targeting of cells expressing CLDN6 such as a therapy using antibodies exerting one or more immune effector functions such as cytotoxic CLDN6 specific antibodies, e.g. antibodies labeled with a cytotoxic substance such as a toxin or a radiolabel or inducing a cell killing mechanism such as CDC or ADCC. Diseases characterized by diseased cells expressing CLDN6 are treatable by a therapy targeting CLDN6 such as cancer diseases, in particular those described herein.

In one embodiment of any of the above aspects, the sample, cellular sample or biological sample is from a patient having a cancer disease, being suspected of having or falling ill with a cancer disease or having a potential for a cancer disease. In one embodiment, the sample, cellular sample or biological sample is from a tissue or organ wherein the cells when the tissue or organ is free of cancer do not substantially express CLDN6. Preferably said tissue is a tissue other than placenta tissue. Preferably, said tissue has already been diagnosed as being affected by a cancer disease, e.g. by visual inspection or culture testing of cells of said tissue or organ. In this embodiment, the presence of CLDN6 or CLDN6-expressing cells and/or a quantity of CLDN6 or CLDN6-expressing cells which is increased compared to a reference level, e.g. compared to a patient without a tumor disease, may indicate that a patient is suitable for a therapy involving the targeting of cells expressing CLDN6.

In one aspect, the invention provides compositions, e.g., diagnostic compositions, or kits, comprising an antibody or antigen-binding fragment or a combination of antibodies and/or or antigen-binding fragments described herein. Such diagnostic compositions or test kits are useful in the methods of the invention such as the methods for diagnosis, detection or monitoring of the invention. These kits may optionally comprise a detectable label, e.g. indicator enzymes, radiolabels, fluorophores, or paramagnetic particles. Kits may include informative pamphlets, for example, pamphlets informing on how to use reagents to practice a method disclosed herein.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IU- PAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "antigen" relates to an agent comprising an epitope against which an immune response is directed and/or is to be generated. Preferably, an antigen in the context of the present invention is a molecule which, optionally after processing, induces an immune reaction, which is preferably specific for the antigen. The term "antigen" includes in particular proteins, peptides, polysaccharides, nucleic acids, especially RNA and DNA, and nucleotides.

The term "epitope" refers to an antigenic determinant in a molecule such as an antigen, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as a CLDN preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "discontinuous epitope" as used herein, means a conformational epitope on a protein antigen which is formed from at least two separate regions in the primary sequence of the protein.

Antigens include tumor-associated antigens, such as CLDN6, i.e., constituents of cancer cells which may be derived from the cytoplasm, the cell surface and the cell nucleus, in particular those antigens which are produced, preferably in large quantity, intracellularly or as surface antigens on cancer cells.

In the context of the present invention, the terms "tumor-associated antigen" or "tumor antigen" relate to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in cancer tissues.

Examples for differentiation antigens which ideally fulfill the criteria for tumor-associated antigens as target structures in tumor immunotherapy, in particular, in tumor vaccination are the cell surface proteins of the claudin family, such as CLDN6. Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm.

The term "claudin 6" or "CLDN6" preferably relates to human CLDN6, and, in particular, to a protein comprising the amino acid sequence according to SEQ ID NO: 1 of the sequence listing or a variant of said amino acid sequence. In respect of CLDN6, the term "variant" in particular refers to a protein comprising the amino acid sequence according to SEQ ID NO: 1 of the sequence listing wherein the Ile at position 143 is replaced by Val. The term "CLDN6" includes any CLDN6 variants such as posttranslationally modified variants and conformation variants.

The term "CLDN9" preferably relates to human CLDN9, and, in particular, to a protein comprising the amino acid sequence according to SEQ ID NO: 2 of the sequence listing or a variant of said amino acid sequence.

The term "CLDN4" preferably relates to human CLDN4, and, in particular, to a protein comprising the amino acid sequence according to SEQ ID NO: 4 of the sequence listing or a variant of said amino acid sequence.

The term "CLDN3" preferably relates to human CLDN3, and, in particular, to a protein comprising the amino acid sequence according to SEQ ID NO: 3 of the sequence listing or a variant of said amino acid sequence.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is detectable and can be targeted in ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

According to the invention, a cell expressing CLDN6 is preferably characterized by cell-surface membrane-bound CLDN6, i.e. CLDN6 is associated with the cell surface. Furthermore, according to the invention, cellular CLDN6 is preferably cell-surface membrane-bound CLDN6. A cell expressing CLDN6 or a cell characterized by association of CLDN6 with its cell surface preferably is a cancer cell, preferably a cancer cell from a cancer described herein.

The term "associated with the cell surface" means that a tumor-associated antigen such as CLDN6 is associated with and located at the plasma membrane of a cell, wherein at least a part of the tumor-associated antigen faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a tumor-associated antigen associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules.

According to the invention, CLDN6 is not substantially expressed in a cell if the level of expression is lower compared to expression in placenta cells or placenta tissue. Preferably, the level of expression is less than 10%, preferably less than 5%, 3%, 2%, 1%, 0.5%, 0.1% or 0.05% of the expression in placenta cells or placenta tissue or even lower. Preferably, CLDN6 is not substantially expressed in a cell if the level of expression exceeds the level of expression in non-cancerous tissue other than placenta by no more than 2-fold, preferably 1.5-fold, and preferably does not exceed the level of expression in said non-cancerous tissue. Preferably, CLDN6 is not substantially expressed in a cell if the level of expression is below the detection limit and/or if the level of expression is too low to allow binding by CLDN6-specific antibodies added to the cells.

According to the invention, CLDN6 is expressed in a cell if the level of expression exceeds the level of expression in non-cancerous tissue other than placenta preferably by more than 2-fold, preferably 10-fold, 100-fold, 1000-fold, or 10000-fold. Preferably, CLDN6 is expressed in a cell if the level of expression is above the detection limit and/or if the level of expression is high enough to allow binding by CLDN6-specific antibodies added to the cells. Preferably, CLDN6 expressed in a cell is expressed or exposed on the surface of said cell.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives of antibodies, including, without limitation, human antibodies, humanized antibodies, chimeric antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The terms "antigen-binding portion" of an antibody (or simply "binding portion") or "antigen-binding fragment" of an antibody (or simply "binding fragment") refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The antibodies described herein may be monoclonal antibodies. The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The antibodies described herein may be recombinant antibodies. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities. Moreover, an isolated antibody may be substantially free of other cellular material and/or chemicals.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 μg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN6 if it is capable of binding to CLDN6 but is not (substantially) capable of binding to other targets, in particular other CLDN proteins such as CLDN9, CLDN4 and/or CLDN3 and/or proteins other than claudin proteins, preferably proteins other than CLDN6. Preferably, an antibody is specific for CLDN6 if the affinity for and the binding to such other targets does not significantly exceed the affinity for or binding to claudin-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, 10 M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The term "compete" refers to the competition between two antibodies for binding to a target antigen. If two antibodies do not block each other for binding to a target antigen, such antibodies are non-competing and this is an indication that said antibodies do not bind to the same part, i.e. epitope, of the target antigen. It is well known to a person skilled in the art how to test for competition of antibodies for binding to a target antigen. An example of such a method is a so-called cross-competition assay, which may e.g. be performed as an ELISA or by flow-cytometry. For example an ELISA-based assay may be performed by coating ELISA plate wells with one of the antibodies; adding the competing antibody and His-tagged antigen/target and detecting whether the added antibody inhibited binding of the His-tagged antigen to the coated antibody, e.g., by adding biotinylated anti-His antibody, followed by Streptavidin-poly-HRP, and further developing the reaction with ABTS and measuring the absorbance at 405 nm. For example a flow-cytometry assay may be performed by incubating cells expressing the antigen/target with an excess of unlabeled antibody, incubating the cells with a sub-optimal concentration of biotin-labelled antibody, followed by incubation with fluorescently labeled streptavidin and analyzing by flow cytometry.

Two antibodies have the "same specificity" if they bind to the same antigen and to the same epitope. Whether an antibody to be tested recognizes the same epitope as a certain antigen-binding antibody, i.e., the antibodies bind to the same epitope, can be tested by different methods known to the skilled person, e.g., based on the competition of the antibodies for the same epitope. The competition between the antibodies can be detected by a cross-blocking assay. For example, a competitive ELISA assay may be used as a cross-blocking assay. For example, target antigen may be coated on the wells of a microtiter plate and antigen-binding antibody and candidate competing test antibody may be added. The amount of the antigen-binding antibody bound to the antigen in the well indirectly correlates with the binding ability of the candidate competing test antibody that competes therewith for binding to the same epitope. Specifically, the larger the affinity of the candidate competing test antibody is for the same epitope, the smaller the amount of the antigen-binding antibody bound to the antigen-coated well. The amount of the antigen-binding antibody bound to the well can be measured by labeling the antibody with detectable or measurable labeling substances.

An antibody competing for binding to an antigen with another antibody, e.g., an antibody comprising heavy and light chain variable regions as described herein, or an antibody having the specificity for an antigen of another antibody, e.g., an antibody comprising heavy and light chain variable regions as described herein, may be an antibody comprising variants of said heavy and/or light chain variable regions as described herein, e.g. modifications in the CDRs and/or a certain degree of identity as described herein.

As used herein, "isotype" refers to the antibody class (e.g., IgM or IgG1) that is encoded by heavy chain constant region genes. Antibodies according to the invention include polyclonal and monoclonal antibodies and include IgG2a (e.g. IgG2a, κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies.

As used herein, "isotype switching" refers to the phenomenon by which the class, or isotype, of an antibody changes from one Ig class to one of the other Ig classes.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention, antibodies may be derived from different species, including but not limited to mouse, rat, rabbit, guinea pig and human. Antibodies also include chimeric molecules in which an antibody constant region derived from one species, preferably human, is combined with the antigen binding site derived from another species. Moreover, antibodies include humanized molecules in which the antigen binding sites of an antibody derived from a non-human species are combined with constant and framework regions of human origin.

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against CLDN6 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity; see e.g. Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies to CLDN6, mice can be immunized with carrier-conjugated peptides derived from the CLDN6 sequence, an enriched preparation of recombinantly expressed CLDN6 antigen or fragments thereof and/or cells expressing CLDN6 or fragments thereof, as described. Alternatively, mice can be immunized with DNA encoding full length human CLDN6 or fragments thereof. In the event that immunizations using a purified or enriched preparation of the CLDN6 antigen do not result in antibodies, mice can also be immunized with cells expressing CLDN6, e.g., a cell line, to promote immune responses.

The immune response can be monitored over the course of the immunization protocol with plasma and serum samples being obtained by tail vein or retroorbital bleeds. Mice with sufficient titers of anti-CLDN6 immunoglobulin can be used for fusions. Mice can be boosted intraperitoneally or intravenously with CLDN6 expressing cells 3-5 days before sacrifice and removal of the spleen to increase the rate of specific antibody secreting hybridomas.

To generate hybridomas producing monoclonal antibodies to CLDN6, cells from lymph nodes, spleens or bone marrow obtained from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using CLDN6 expressing cells, antibodies with specificity for CLDN6 can be identified. The antibody secreting hybridomas can be replated, screened again, and if still positive for anti-CLDN6 monoclonal antibodies can be subcloned by limiting dilution. The stable subclones can then be cultured in vitro to generate antibody in tissue culture medium for characterization.

Antibodies of the invention can also be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment, chimeric antibodies are generated by joining human kappa-light chain constant region to murine light chain variable region. In an also preferred embodiment, chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual positions evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas may be used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are described. The plasmids can be constructed so that PCR amplified V heavy and V kappa light chain cDNA sequences can be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-CLDN6 antibodies described herein, are used to create structurally related humanized anti-CLDN6 antibodies that retain at least one functional property of the antibodies of the invention, such as binding to CLDN6. More specifically, one or more CDR regions of mouse monoclonal antibodies can be combined recombinantly with known human framework regions and CDRs to create additional, recombinantly-engineered, humanized anti-CLDN6 antibodies.

The ability of an antibody to bind CLDN6 can be determined using standard binding assays, e.g., ELISA, Western Blot, Immunofluorescence and Flow cytometric analysis.

ELISA can be used to demonstrate the presence of antibodies in sera of immunized mice or binding of monoclonal antibodies to CLDN6 protein or peptides. Peptides or protein used for immunization may be used for determining the specificity of hybridoma supernatants or analysing serum titers.

In order to demonstrate presence of antibodies in sera of immunized mice or binding of monoclonal antibodies to living cells, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of anti-CLDN6 antibodies in sera of immunized mice or binding of monoclonal antibodies to living cells expressing CLDN6, immunofluorescence microscopy analysis can be used. For example, cell lines expressing either spontaneously or after transfection CLDN6 and negative controls lacking CLDN6 expression are grown in chamber slides under standard growth conditions in DMEM/F12 medium, supplemented with 10% fetal calf serum (FCS), 2 mM L-glutamine, 100 IU/ml penicillin and 100 μg/ml streptomycin. Cells can then be fixed with methanol or paraformaldehyde or left untreated. Cells can then be reacted with monoclonal antibodies against CLDN6 for 30 min. at 25° C. After washing, cells can be reacted with an Alexa555-labelled anti-mouse IgG secondary antibody (Molecular Probes) under the same conditions. Cells can then be examined by fluorescence microscopy.

Total CLDN6 levels in cells can be observed when cells are methanol fixed or paraformaldehyde fixed and permeabilized with Triton X-100. In living cells and non-permeabilized, paraformaldehyde fixed cells surface localization of CLDN6 can be examined. Additionally targeting of CLDN6 to tight junctions can be analyzed by co-staining with tight junction markers such as ZO-1. Furthermore, effects of antibody binding and CLDN6 localization within the cell membrane can be examined.

Anti-CLDN6 IgG can be further tested for reactivity with CLDN6 antigen by Western Blotting. Briefly, cell extracts from cells expressing CLDN6 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Anti-CLDN6 mouse IgGs can be further tested for reactivity with CLDN6 antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection with CLDN6. For immunostaining, antibodies reactive to CLDN6 can be incubated followed by horseradish-peroxidase conjugated goat anti-mouse or goat anti-rabbit antibodies according to the vendors instructions.

One particularly preferred methodology for assaying CLDN6 in the methods of the invention is Immunohistochemistry or IHC. Immunohistochemistry or IHC refers to the process of detecting antigens (e.g., proteins) in cells of a tissue section, e.g. cells of the tissues mentioned herein. Immunohistochemical staining is widely used in the diagnosis of abnormal cells such as those found in cancerous tumors. Visualising an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as fluorescein or rhodamine.

Preparation of the sample is critical to maintain cell morphology, tissue architecture and the antigenicity of target epitopes. This requires proper tissue collection, fixation and sectioning. Paraformaldehyde is usually used with fixation. Depending on the purpose and the thickness of the experimental sample, either thin (about 4-40 μm) sections are sliced from the tissue of interest, or if the tissue is not very thick and is penetrable it is used whole. The slicing is usually accomplished through the use of a microtome, and slices are mounted on slides.

The sample may require additional steps to make the epitopes available for antibody binding, including deparaffinization and antigen retrieval. Detergents like Triton X-100 are generally used in Immunohistochemistry to reduce surface tension, allowing less reagent to be used to achieve better and more even coverage of the sample.

The direct method of immunohistochemical staining uses one labelled antibody, which binds directly to the antigen being stained for. The indirect method of immunohistochemical staining which is more common uses one antibody against the antigen being probed for, and a second, labelled, antibody against the first.

To reduce background staining in IHC, the samples are incubated with a buffer that blocks the reactive sites to which the primary or secondary antibodies may otherwise bind. Primary antibodies are raised against an antigen of interest and are typically unconjugated (unlabelled), while secondary antibodies are raised against immunoglobulins of the primary antibody species. The secondary antibody is usually conjugated to a linker molecule, such as biotin, that then recruits reporter molecules, or the secondary antibody is directly bound to the reporter molecule itself. Common blocking buffers include normal serum, non-fat dry milk, BSA or gelatin, and commercial blocking buffers.

Reporter molecules vary based on the nature of the detection method, and the most popular methods of detection are with enzyme- and fluorophore-mediated chromogenic and fluorescence detection, respectively. With chromogenic reporters, an enzyme label is reacted with a substrate to yield an intensely colored product that can be analyzed with an ordinary light microscope. While the list of enzyme substrates is extensive, alkaline phosphatase (AP) and horseradish peroxidase (HRP) are the two enzymes used most extensively as labels for protein detection. An array of chromogenic, fluorogenic and chemiluminescent substrates is available for use with either enzyme, including DAB or BCIP/NBT. Fluorescent reporters are small, organic molecules used for IHC detection. For chromogenic and fluorescent detection methods, densitometric analysis of the signal can provide semi- and fully-quantitative data, respectively, to correlate the level of reporter signal to the level of protein expression or localization.

After immunohistochemical staining of the target antigen, a second stain is often applied to provide contrast that helps the primary stain stand out. Many of these stains show specificity for discrete cellular compartments or antigens, while others will stain the whole cell. Both chromogenic and fluorescent dyes are available for IHC to provide a vast array of reagents to fit every experimental design. Hematoxylin, Hoechst stain and DAPI are commonly used.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The term "immune effector functions" in the context of the present invention includes any functions mediated by components of the immune system that result in the inhibition of tumor growth and/or inhibition of tumor development, including inhibition of tumor dissemination and metastasis. Preferably, immune effector functions result in killing of cancer cells. Preferably, the immune effector functions in the context of the present invention are antibody-mediated effector functions. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, for example, by binding of the antibody to a surface antigen, inhibition of CD40L-mediated signal transduction, for example, by binding of the antibody to the CD40 receptor or CD40 ligand (CD40L), and/or inhibition of proliferation of the cells carrying the tumor-associated antigen, preferably ADCC and/or CDC. Thus, antibodies that are capable of mediating one or more immune effector functions are preferably able to mediate killing of cells by inducing CDC-mediated lysis, ADCC-mediated lysis, apoptosis, homotypic adhesion, and/or phagocytosis, preferably by inducing CDC-mediated lysis and/or ADCC-mediated lysis. Antibodies may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

ADCC describes the cell-killing ability of effector cells, in particular lymphocytes, which preferably requires the target cell being marked by an antibody. ADCC preferably occurs when antibodies bind to antigens on cancer cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and further host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple Clq binding sites in close proximity on the CH2 domains of participating antibody molecules such as IgG molecules (Clq is one of three subcomponents of complement C1). Preferably these uncloaked Clq binding sites convert the previously low-affinity Clq-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

The term "immune effector cells" in the context of the present invention relates to cells which exert effector functions during an immune reaction. For example, such cells secrete cytokines and/or chemokines, kill microbes, secrete antibodies, recognize cancerous cells, and optionally eliminate such cells. For example, immune effector cells comprise T-cells (cytotoxic T-cells, helper T-cells, tumor infiltrating T-cells), B-cells, natural killer cells, neutrophils, macrophages, and dendritic cells.

A nucleic acid is according to the invention preferably deoxyribonucleic acid (DNA) or ribonucleic acid (RNA), more preferably RNA, most preferably in vitro transcribed RNA (IVT RNA). Nucleic acids include according to the invention genomic DNA, cDNA, mRNA, recombinantly prepared and chemically synthesized molecules. A nucleic acid may according to the invention be in the form of a molecule which is single stranded or double stranded and linear or closed covalently to form a circle. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

The nucleic acids described herein may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

As the vector for expression of an antibody, either of a vector type in which the antibody chains are present in different vectors or a vector type in which the antibody chains are present in the same vector can be used.

As used herein, the term "RNA" means a molecule comprising ribonucleotide residues. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region, a protein or peptide coding region and a 3' non translated region. mRNA has a limited halftime in cells and in vitro.

In the context of the present invention, the term "transcription" relates to a process, wherein the genetic code in a DNA sequence is transcribed into RNA.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

The term "expression" is used herein in its broadest meaning and comprises the production of RNA or of RNA and protein or peptide. With respect to RNA, the term "expression" or "translation" relates in particular to the production of peptides or proteins. Expression may be transient or may be stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor-associated antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor-associated antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue is specifically expressed in cells of the gastric mucosa. In some embodiments, a tumor-associated antigen may also be specifically expressed under normal conditions in more than one tissue type or organ, such as in 2 or 3 tissue types or organs, but preferably in not more than 3 different tissue or organ types. In this case, the tumor-associated antigen is then specifically expressed in these organs.

The term "translation" according to the invention relates to the process in the ribosomes of a cell by which a strand of messenger RNA directs the assembly of a sequence of amino acids to make a protein or peptide.

According to the invention, the term "nucleic acid encoding" means that nucleic acid, if present in the appropriate environment, preferably within a cell, can be expressed to produce a protein or peptide it encodes.

The term "peptide" comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

The teaching given herein with respect to specific amino acid sequences, e.g. those shown in the sequence listing, is to be construed so as to also relate to modifications, i.e. variants, of said specific sequences resulting in sequences which are functionally equivalent to said specific sequences, e.g. amino acid sequences exhibiting properties identical or similar to those of the specific amino acid sequences. One important property is to retain binding of an antibody to its target. Preferably, a sequence modified with respect to a specific sequence, when it replaces the specific sequence in an antibody retains binding of said antibody to the target.

It will be appreciated by those skilled in the art that in particular the sequences of the CDR sequences, hypervariable and variable regions can be modified without losing the ability to bind to a target. For example, CDR sequences will be either identical or highly homologous to the CDR sequences specified herein.

By "highly homologous" it is contemplated that from 1 to 5, preferably from 1 to 4, such as 1 to 3 or 1 or 2 substitutions may be made.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS: needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased or decreased immunogenicity.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). Mammalian cells are particularly preferred, such as cells from humans, mice, hamsters, pigs, goats, and primates. The cells may be derived from a large number of tissue types and include primary cells and cell lines. The term "cell" includes non-cancerous cells and cancer cells such as cells of the cancer types disclosed herein.

A cell which comprises a nucleic acid molecule preferably express the peptide or protein encoded by the nucleic acid.

"Target cell" shall mean a cell which is a target for an immune response such as an antibody. Target cells include any undesirable cell such as a cancer cell as described herein. In preferred embodiments, the target cell is a cell expressing CLDN6. Cells expressing CLDN6 typically include cancer cells.

The terms "transgenic animal" refers to an animal having a genome comprising one or more transgenes, preferably antibody heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN6 antibodies when immunized with CLDN6 antigen and/or cells expressing CLDN6. The human heavy chain transgene can be integrated into the chromosomal DNA of the mouse, as is the case for transgenic mice, e.g., HuMAb mice, such as HCo7 or HCol2 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN6 (e.g., IgG, IgA and/or IgE) by undergoing V-D-J recombination and isotype switching.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral immune reaction, the strength and/or duration of the induced immune reaction, or the specificity of the immune reaction. In the context of the present invention, the term "immunologically equivalent" is preferably used with respect to the immunological effects or properties of a peptide or peptide variant used for immunization or an antibody. A particular immunological property is the ability to bind to antibodies and, where appropriate, generate an immune response, preferably by stimulating the generation of antibodies. For example, an amino acid sequence is immunologically equivalent to a reference amino acid sequence if said amino acid sequence when exposed to the immune system of a subject induces an immune reaction, preferably antibodies, having a specificity of reacting with the reference amino acid sequence, such as the reference amino acid sequence forming part of CLDN6.

The invention provides methods for detecting the presence of CLDN6 antigen in a sample, or measuring the amount of CLDN6 antigen, comprising contacting the sample, and optionally a control sample, with an antibody of the invention which binds to CLDN6, under conditions that allow for formation of a complex between the antibody and CLDN6. The formation of a complex is then detected, wherein a difference in complex formation between the sample compared to a control sample is indicative for the presence of CLDN6 antigen in the sample.

Methods as described above are useful, in particular, for diagnosing CLDN6-related diseases such as cancer diseases, e.g., cancer diseases as described herein. Preferably an amount of CLDN6 in a sample which is higher than the amount of CLDN6 in a reference or control sample is indicative for the presence of a CLDN6-related disease in a subject, in particular a human, from which the sample is derived.

When used in methods as described above, an antibody described herein may be provided with a label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the invention, a "reference" such as a reference sample or reference organism may be used to correlate and compare the results obtained in the methods of the invention from a test sample or test organism. Typically the reference organism is a healthy organism, in particular an organism which does not suffer from a disease such as a cancer disease. A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to diagnose a subject with a disease. Diseases which can be diagnosed encompass all diseases expressing CLDN6. Particularly preferred diseases are cancer diseases such as cancer diseases described herein.

According to the invention, the term "disease" refers to any pathological state, including cancer diseases, in particular those forms of cancer diseases described herein.

The term "normal" such as used in the terms "normal tissue" or "normal conditions" refers to healthy tissue or the conditions in a healthy subject, i.e., non-pathological conditions, wherein "healthy" preferably means non-cancerous.

"Disease involving cells expressing CLDN6" means according to the invention that CLDN6 is expressed in cells of a diseased tissue or organ. In one embodiment, expression of CLDN6 is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing CLDN6 include cancer diseases, in particular those forms of cancer described herein.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize). Common examples of benign tumors include moles and uterine fibroids.

The term "benign" implies a mild and nonprogressive disease, and indeed, many kinds of benign tumors are harmless to the health. However, some neoplasms which are defined as "benign tumors" because they lack the invasive properties of a cancer, may still produce negative health effects. Examples of this include tumors which produce a "mass effect" (compression of vital organs such as blood vessels), or "functional" tumors of endocrine tissues, which may overproduce certain hormones (examples include thyroid adenomas, adrenocortical adenomas, and pituitary adenomas).

Benign tumors typically are surrounded by an outer surface that inhibits their ability to behave in a malignant manner. In some cases, certain "benign" tumors may later give rise to malignant cancers, which result from additional genetic changes in a subpopulation of the tumor's neoplastic cells. A prominent example of this phenomenon is the tubular adenoma, a common type of colon polyp which is an important precursor to colon cancer. The cells in tubular adenomas, like most tumors which frequently progress to cancer, show certain abnormalities of cell maturation and appearance collectively known as dysplasia. These cellular abnormalities are not seen in benign tumors that rarely or never turn cancerous, but are seen in other pre-cancerous tissue abnormalities which do not form discrete masses, such as pre-cancerous lesions of the uterine cervix. Some authorities prefer to refer to dysplastic tumors as "pre-malignant", and reserve the term "benign" for tumors which rarely or never give rise to cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. According to the invention, the terms "cancer" and "tumor" or "cancer disease" and "tumor disease" are generally used interchangeably herein to refer to diseases wherein cells display an uncontrolled growth and optionally invasion and/or metastasis.

Preferably, a "cancer disease" according to the invention is characterized by cells expressing CLDN6. A cell expressing CLDN6 preferably is a cancer cell, preferably of the tumors and cancers described herein. Preferably, such cell is a cell other than a placenta cell.

Cancers are classified by the type of cell that resembles the tumor and, therefore, the tissue presumed to be the origin of the tumor. These are the histology and the location, respectively.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a cancer disease, has received a successful treatment of said disease and again develops said disease said newly developed disease may be considered as relapse or recurrence. However, according to the invention, a relapse or recurrence of a cancer disease may but does not necessarily occur at the site of the original cancer disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor. Immunotherapy may be performed using any of a variety of techniques, in which agents function to remove antigen-expressing cells from a patient.

Within certain embodiments, immunotherapy may be active immunotherapy, in which treatment relies on the in vivo stimulation of the endogenous host immune system to react against diseased cells with the administration of immune response-modifying agents (such as immunoreactive peptides and nucleic acids).

Within other embodiments, immunotherapy may be passive immunotherapy, in which treatment involves the delivery of agents with established tumor-immune reactivity (such as antibodies) that can directly or indirectly mediate antitumor effects and does not necessarily depend on an intact host immune system.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

According to the invention, a "sample" may be any sample useful according to the present invention, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates. Preferably a sample contains cells or tissue of the organ which is to be examined, e.g. which is to be diagnosed for cancer. For example, if the cancer to be diagnosed is lung cancer a sample may contain cells or tissue obtained from lung.

According to the invention a sample may be a sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells.

The present invention is described in detail by the figures and examples below, which are used only for illustration purposes and are not meant to be limiting. Owing to the description and the examples, further embodiments which are likewise included in the invention are accessible to the skilled worker.

BRIEF DESCRIPTION OF THE DRAWINGS

FIG. 1A: Sequence alignment of claudin 6 and claudin 9 proteins (human/murine)

The sequence alignment shows the high homology between human and mouse claudin 6 and human claudin 9.

FIG. 1B: Sequence alignment of claudin 6 and claudin 3, 4 and 9 proteins (human)

The sequence alignment shows the high homology in the claudin multigene family

Figure 2A:
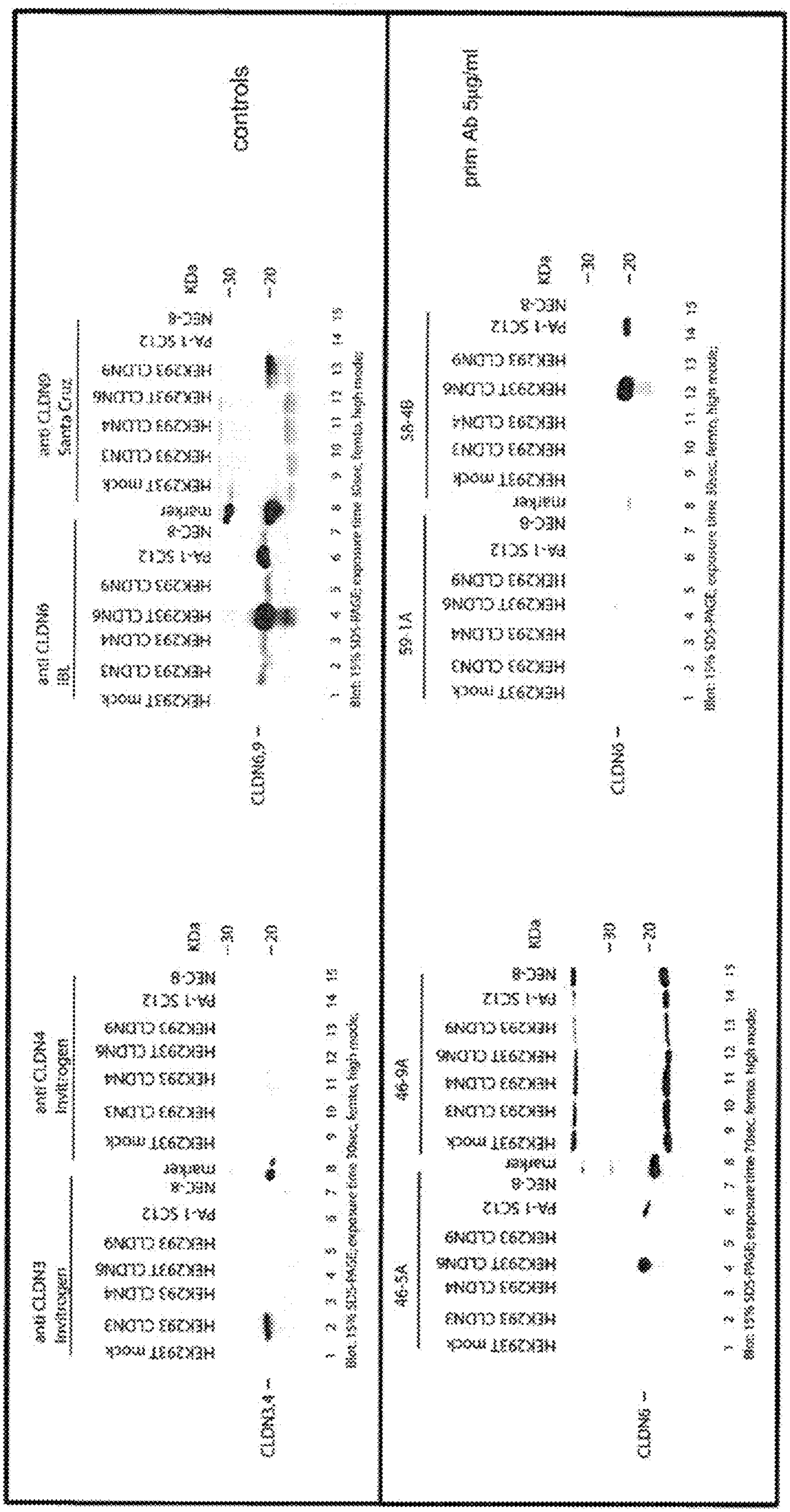

FIGS. 2A and B: Specificity of antibodies tested in WesternBlot analysis

Cell lysates of HEK293 cells transfected with mock, human CLDN3, 4, 6 or 9 and CLDN6 positive tumor cells (PA-1 SC12 and NEC-8) were blotted and bound antibodies (rabbit-anti-CLDN3 (Invitrogen) 0.5 μg/mL, mouse-anti-CLDN4 (Invitrogen) 1 μg/mL, rabbit-anti-CLDN6 (IBL) 0.2 μg/mL, goat-anti-CLDN9 (Santa Cruz) 0.4 μg/mL or the monoclonal mouse antibodies (5 μg/mL) were detected by Peroxidase-conjugated secondary antibodies.

Figure 3:
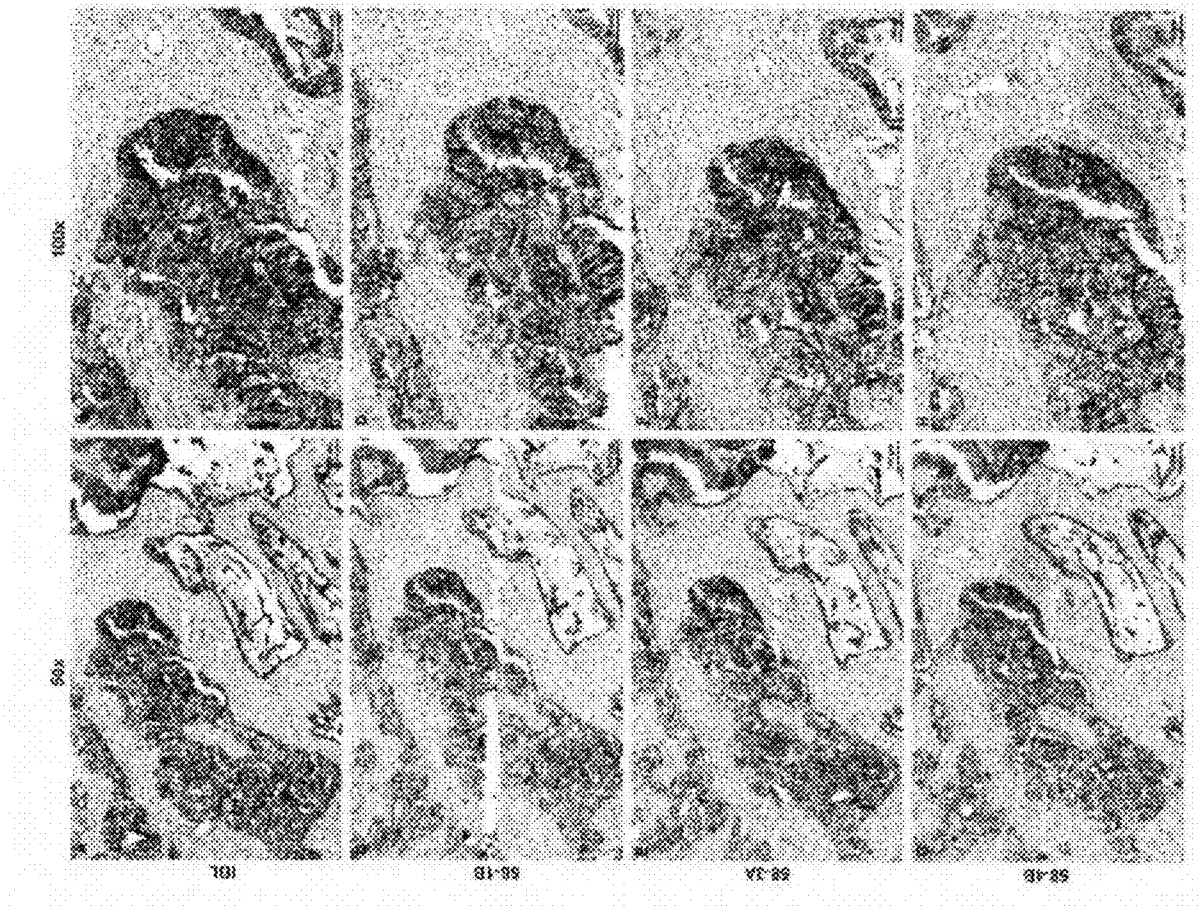

FIG. 3: Histological analysis of Western Blot positive antibodies

Binding of lead mumAB 58-1B, 58-3A and 58-4B in comparison to rb-anti-CLDN6 IBL antiserum to FFPE sections of ovarian cancer.

Figure 4A:
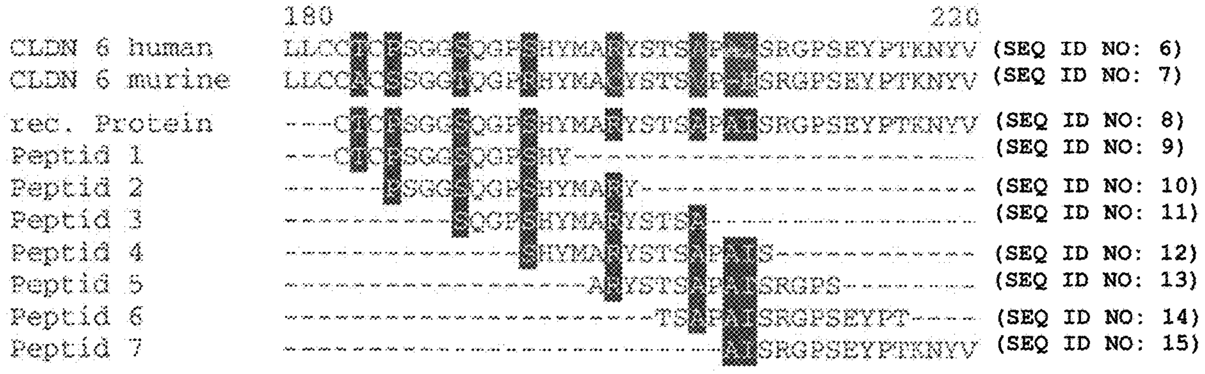

FIG. 4A: Epitope Mapping using synthetic overlapping peptides

Overlapping peptides were immobilized onto microtiter plates and antibodies were added. Bound antibodies were developed with appropriate peroxidase conjugated secondary reagents.

FIG. 4B: Epitope Mapping using biotinylated synthetic overlapping peptides

Highly overlapping peptides N-terminally biotinylated via a flexible hydrophilic linker were synthesized and loaded onto StrepAvidin coupled microtiter plates. Antibodies (1 μg/mL) were applied and bound antibodies were detected and analysed.

For comparison of signal intensities of mumAB 58-4B-2 to rb-serum (IBL) maximal binding of antibodies to C-term peptide 19 was defined as 100%.

Binding intensity of each antibody to one peptide was calculated relative to maximal binding for each test system.

Binding of mumABs was analysed in 3 independent experiments in triplicates

Binding of IBL-serum was analysed in 2 independent experiments in triplicates

Figure 4C:
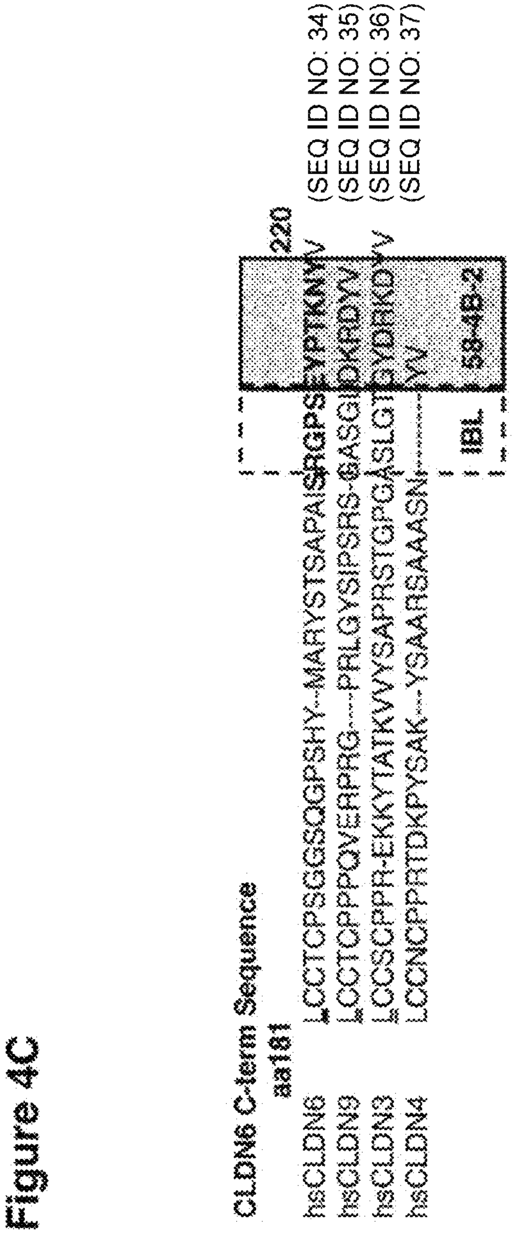

FIG. 4C: Binding site of monoclonal lead 58-4B-2 and polyclonal rb-antiCLDN6-serum (IBL).

FIG. 5: Sequences of the antibodies 58-1B, 58-3A and 58-4B

Figure 6:
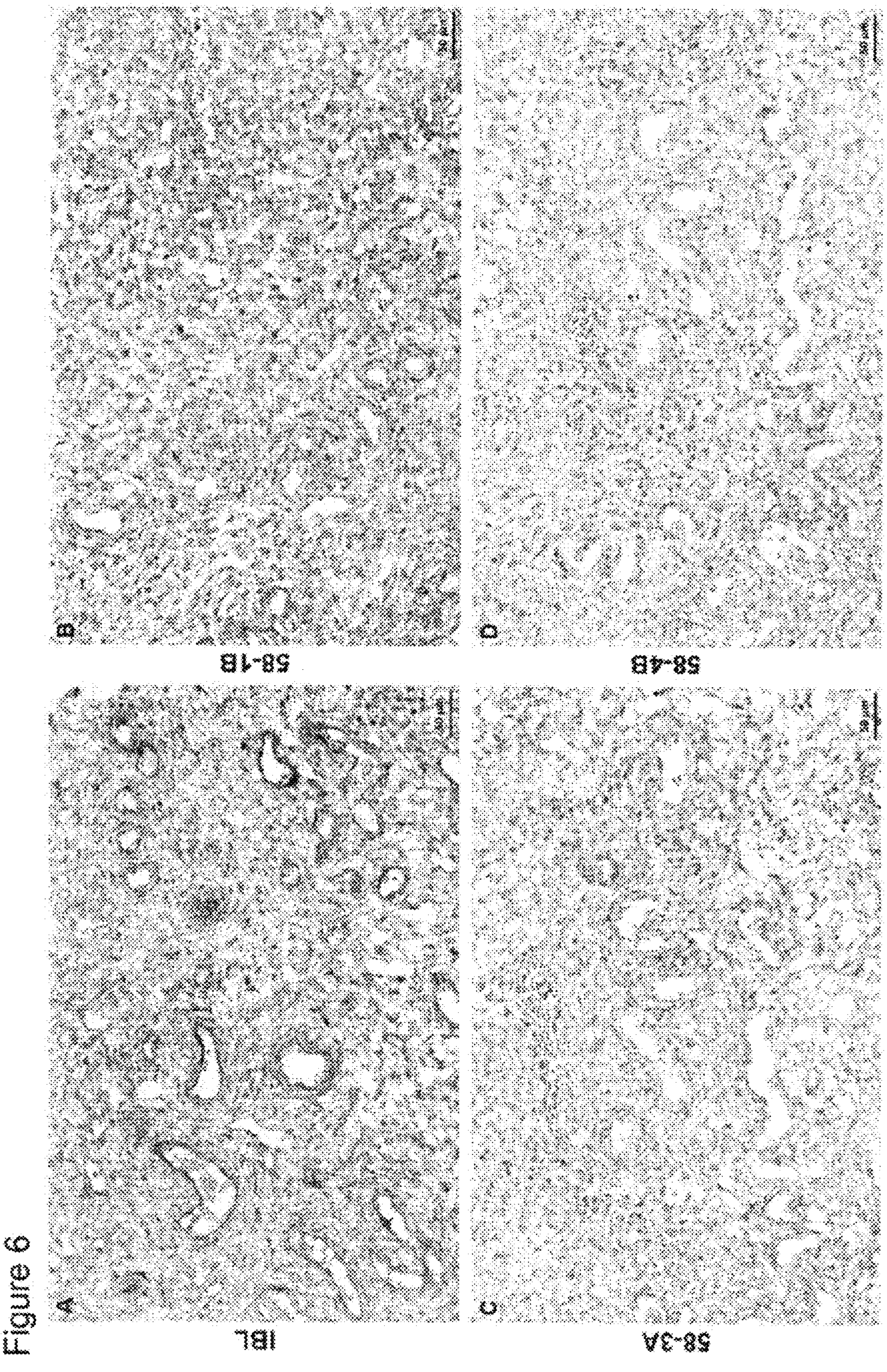

FIG. 6: Background signals of different antibodies on normal ovarian tissue

Comparison of the lead antibodies mumAB 58-1B, 58-3A and 58-4B versus the commercial IBL antibody on normal ovarian tissue (antibody concentration 5 μg/ml; clinic-like protocol).

FIG. 7: Indications relating to deposited microorganism or other biological material Identification of deposit for Accession Number DSM ACC3311 (Mouse (*Mus musculus*) myeloma Ag8.653 fused with mouse (*Mus musculus*) splenocytes; Hybridoma secreting antibody against human CLDN6).

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Mapping of Antibody Binding Site (FIG. 4A)

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

Epitope Mapping with Biotinylated Peptides (FIG. 4B)

A Peptide-ELISA was performed to identify the antibody-binding site of monoclonal murine lead antibodies and polyclonal rb-serum from IBL. Biotinylated overlapping peptides covering the C-terminal sequence of CLDN6 were coupled to SA coated plates. Purified mumAB (1 μg/ml) or IBL rb-serum (1 μg/ml) were applied to antigen coated ELISA-plates and unbound antibodies were washed off. Bound antibodies were detected with corresponding enzyme-labeled secondary antibody (alkaline phosphatase goat anti-mouse IgG(1+2a+2b+3) or alkaline phosphatase goat anti-rabbit IgG F(ab)2) and ABTS enzyme substrate and signal intensities are analysed.

For comparison of signal intensities of mumAB 58-4B-2 to rb-serum (IBL) maximal binding of antibodies to C-term peptide19 was defined as 100%.

Binding intensity of each antibody to one peptide was calculated in relation to maximal binding for each test system (mouse or rabbit) independently.

Binding of mumABs were analysed in 3 independent experiments in triplicates

Binding of IBL-serum was analysed in 2 independent experiments in triplicates

Isotype Determination

To determine the isotype of purified antibodies, the IsoStrip Mouse Monoclonal Antibody Isotyping Kit (Roche, Cat. No. 1493027) was used as described by the manufacturer.

Western Blot

Newly generated Anti-CLDN6 IgG can be further tested for specific binding to CLDN6 antigen by Western Blotting. Briefly, cell extracts from cells expressing CLDN3, 4, 6 or 9 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Histology

Immunohistochemistry (IHC) was performed on slides of 4% buffered formalin fixed paraffin embedded tissue samples. Paraffin embedding was performed according to standard protocols.

After deparaffinization and rehydration, all slides were subjected to antigen retrieval by boiling in 0.1 M Tris/0.01 M EDTA buffer supplemented with 15 mM sodium azide (pH 9.0) at 95-98° C. for 30 min, and subsequently endogenous peroxidases were quenched by adding 3% $H_2O_2$ supplemented with 15 mM $NaN_3$. After washing with 150 mM sodium chloride buffer (pH 7.6) supplemented with 0.05% (w/v) Tween-20 and 0.005% (w/v) Proclin, the slides were incubated with 1.0 or 5.0 μg/ml diagnostic monoclonal mouse anti-CLDN6 antibody 58-4B at room temperature for one hour. Antibody binding was visualized using ready-to-use solution containing a polymer-based horseradish-peroxidase-labeled secondary antibody (Histofine MAX PO (M)/UIO MAX PO (M), Nichirei, Japan). Sections were subsequently counter-stained with Mayer's haematoxylin (Carl Roth GmbH, Karlsruhe, Germany) and subjected to evaluation by the raters.

Histological Assessment

All samples were analyzed regarding the relative proportion of positive stained tumour cells in relation to all visible tumour cells for each section. The intensity of the staining was classified as negative (−), weakly positive (1+), medium positive (2+) and strongly positive (3+). Only membranous staining was considered as positive. Ovarian cancer tissue served as positive control for each staining. Additionally embryonic kidney tissue of New Zealand White rabbits on day 29 of the gestation period was found to show a strong positive staining intensity. This was used as internal staining intensity reference for staining positivity (2+-3+).

Example 2: Generation of Monoclonal Antibodies

The aim of this project was to generate murine monoclonal CLDN6-specific antibodies capable of detecting CLDN6 expressing tumour cells in ovarian cancer or any other cancer tissue of any histology including primary peritoneal or fallopian tube tumours FFPE tissues.

To generate a highly specific, high affinity diagnostic CLDN6 antibody it was essential to start immunization protocols with a variety of different immunogens (Table 1) and adjuvants. During the project about 130 mice (C57BL/6 and BALB/c) were subjected to various immunization strategies to trigger an α-CLDN6 immune response (Table 2).

To trigger the mouse immune system and to overcome the immune tolerance we used peptide-conjugates and recombinant proteins coding for different parts of human CLDN6 expressed as recombinant fusion proteins with different epitopes to facilitate affinity purification (Polyhistidine-(HIS)- and Glutathion-S-transferase-(GST)-tag) (Table 1).

Out of 20 different immunization strategies the best results were achieved by treating mice with GST-tagged CLDN6 C-terminal recombinant protein (Table 2) in combination with various adjuvants (Table 2).

On the day of fusion, mouse splenocytes were isolated and fused to the mouse myeloma cell line P3X63Ag8.653 (ATCC). For fusion of mouse cells to the myeloma cell line we followed the standard protocol published by Köhler and Milstein 1975. After hypoxanthine-aminopterin-thymidine (HAT) selection, supernatants were tested in ELISA for secretion of antibodies recognizing the antigen used for immunizations.

69 fusions were performed and more than 25 000 hybridoma cell clones were screened. The hybridoma cells of ELISA positive supernatants (402) were subcloned to generate monoclonal hybridomas. Supernatants of the subcloned hybridoma cells were rescreened in ELISA for binding to Claudin6 antigen. Hybridoma cells of 88 positive clones (binding to antigen but not to backbone or tag) were expanded and supernatants analyzed further in Western Blot for their specificity.

The three lead candidates (58-4B, 58-1B and 58-3A) resulted from a 11 step-immunization strategy (Immunization #10 for 123 days). Three days before splenectomy, the mice were boosted to activate the targeted B-cells followed by fusion 58 (Table 3).

Example 3: Western Blot Screening of Monoclonal Antibodies

Figure 2B:
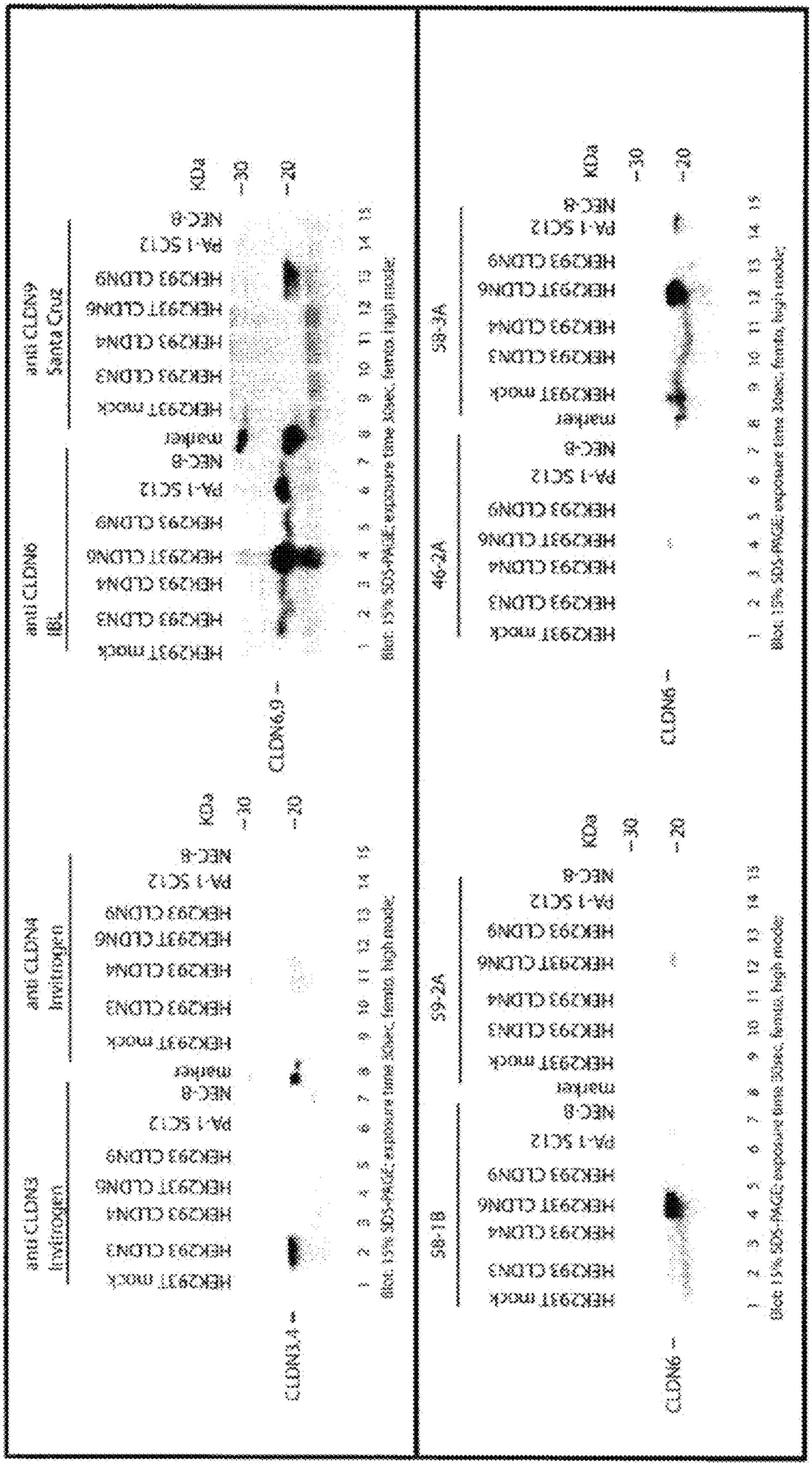

To test if ELISA-positive antibodies in the supernatants are able to bind specifically to recombinant claudin 6 they were analysed in Western Blot. Antibodies binding to CLDN6 but not to any other tagged-protein were purified and cells expanded and cryoconserved. Antibodies were purified via FPLC using MABselect Protein A affinity resin. The purified antibodies selected by the Western Blot screening were reanalyzed in Western Blot to assess the binding to CLDN6 positive tumour cell lines (PA-1, NEC-8) and to CLDN3, 4, 6 or 9 transfected HEK293 cells (FIG. 2). In addition, the antibodies were evaluated for their ability to bind their antigen in formalin fixed paraffin-embedded tissues (FFPE) by immunohistochemistry. Supernatants of 33 hybridoma specifically binding to Claudin 6 were purified and analysed further in Immunohistochemistry.

Example 4: Histological Analysis of Western Blot Positive Antibodies

The aim of this experiment was to test the CLDN6 specificity and sensitivity of the antibodies. This was done by using CLDN6 expressing FFPE ovarian cancer tissues (FIG. 3).

In a first experiment the purified antibodies that were tested positive in the 1st Western Blot-Screen, were analyzed at a concentration of 1 μg/ml and 5 μg/ml on ovarian cancer FFPE sections. A laboratory standard and established overnight staining protocol with Citric retrieval buffer and a retrieval temperature of 120° C. was used. Antibodies showing tissue specific CLDN6 staining without producing high levels of unspecific background staining were further titrated to 0.2, 1, 2 and 5 μg/ml on various ovarian cancer tissues to further evaluate the sensitivity and specificity of these antibodies. In the following development stages the newly generated antibodies were tested directly at higher concentrations of 1 and 5 μg/ml because the differences in staining intensities of the different antibodies could not be clearly evaluated at a concentration of 0.2 μg/ml. Antibodies generating strong signals on the cell membranes of ovarian tumour tissue of the selected tissues and little to no background on the adjacent healthy tissues were selected for further titration experiments and specificity analysis. The following three antibodies fulfilled these criteria and were selected as lead candidates for further investigation: 58-1B, 58-3A and 58-4B.

Example 5: Epitope Mapping of the mumAbs (FIG. 4)

Peptide ELISA was performed to identify the antibody-binding epitopes on CLDN6. Each purified antibody was tested on peptides overlapping 11aa covering the C-terminal sequence of CLDN6. Antibodies 46-5A, 58-1B, 58-3A, 58-4B and 58-9B showed specific binding to an epitope covered by the peptide AISRGPSEYPTKNYV (Peptide 7; FIG. 4A). The binding site of these antibodies was further characterized using biotinylated peptides overlapping by 14 out of 15 aa.

Surprisingly, antibodies 58-1B, 58-3A and 58-4B and subclone 58-4B-2 binding to the sequence EYPTKNY (FIG. 4B) are able to bind to CLDN6 in FFPE cancer tissues very specifically with low background. In contrast, the antibody 46-5A was able to bind to peptides not comprising the sequence EYPTKNY but comprising a portion thereof, i.e. the sequence EYPTK (FIG. 4B). Commercially available rb-anti-CLDN6 polyclonal antiserum (IBL) binds to peptides comprising the sequence RGPS (FIG. 4C).

Example 6: Analysis of Antibody Specificity Using a Normal Tissue Panel

Antibodies producing strong signals on the tested ovarian cancer tissue (58-1B, 58-3A and 58-4B) with the laboratory standard and established staining protocol were further analyzed on various, relevant normal, meaning healthy donor tissues (e.g. lung, testis, uterus und ovar) to ensure the high CLDN6 target specificity. Staining of these selected tissues was performed using the laboratory standard and established staining protocol (overnight; 120° C. retrieval temperature, citric retrieval buffer).

None of the three selected antibodies generated unspecific staining signals on the tested normal tissue panel, except of a faint unspecific signals in a single peripheral region of one ovarian tissue sample. This weak signal was only visible at the higher of both tested concentrations (1 & 5 μg/ml), not representing an ovarian substructure.

Example 7: Comparison of Antibody Sensitivity Using Ovarian Cancer and Normal Tissue Panel Samples No significant differences in the staining pattern and staining intensities of the antibodies 58-3A, 58-1B and 58-4B were visible in the previous experiments. Therefore the antibodies were subjected to staining experiments with a more clinically oriented, meaning more time efficient, staining protocol. To simulate the staining processes applied in standard pathology laboratories, a One-Day-Protocol with an 1 hour primary antibody incubation step and a water bath (98° C.) retrieval step was established. In addition, two different retrieval buffers were compared to test whether the different retrieval conditions could influence the sensitivity of the tested antibodies regarding CLDN6 detection.

For all antibodies more intense signals and a higher amount of positive stained tumour cells were generated with the adapted One-Day-Protocol with Tris-buffer for retrieval, compared to the standard citric retrieval buffer. Most intense staining signals were generated with 58-4B reaching up to 80% of 3+ stained tumor cells, whereas the staining intensities of the candidate 58-1B were the least intense reaching only 30% of 3+ stained tumor cells.

The staining protocol with the Tris-buffer for retrieval resulting in the most sensitive staining signals was subsequently applied for the staining of the normal tissue panel to test the specificity of the selected antibodies under routine clinical laboratory conditions.

The best results in respect to CLDN6-specificity and sensitivity in FFPE-tissues were achieved by using the 58-4B diagnostic antibody candidate. No signals were detectable on the normal tissues. All other antibodies generated signals on Reinke crystals of the testis sample. In addition the 58-3A antibody generated weak staining on blood vessels. The 58-1B antibody demonstrated more intense signals (1+) on testis, and ovarian normal tissues.

In all analyzed samples the mumAb 58-4B demonstrated better performance in respect of showing no background staining and intense staining on relevant tumour tissue, whereas mumAb 58-3A and 58-1B candidates showed intense staining on relevant tumour tissue but with higher background signals. Especially the signals produced using mumAb 58-1B were of high intensity but with the drawback of high background staining.

For the later use in a clinical setting the corresponding hybridoma for generation of the diagnostic antibody candidates were adapted to serum free media. Unfortunately the adaption of clone 58-3A to serum-free conditions wasn't possible. Therefore the antibody candidate 58-3A was also excluded from further histological studies, leaving 58-4B as the final lead candidate.

Example 8: Histological in Depth Analysis and Antibody Characterization

In a first step, the 58-4B antibody lot produced under serum free conditions was compared with the antibody lot produced under serum conditions using a normal tissue panel TMA (MNO961) in order to detect differences in the target-sensitivity and -specificity between the lots. The staining was performed using a clinic like, One-Day-Protocol (waterbath retrieval, Tris-buffer for retrieval) with royalty-free components. With both antibody lots, faint stainings were detected in some normal tissue samples (see Table 4). Compared with the antibody produced under serum conditions, the serum-free antibody lot was cleaner with less artificial spots on the analysed samples. On testis, staining signals were visible on Reinke crystals with both antibody lots.

In a second step, the serum-free produced antibody was tested on an ovarian cancer TMA panel and compared with the commercially available IBL antibody. This commercial antibody had already been used in previous study stainings. The polyclonal IBL antibody was used with the study protocol (overnight, 120° C. retrieval temperature, citric retrieval buffer). The 58-4B antibody was used with the routine clinic like protocol (One-Day-Protocol, waterbath retrieval, Tris buffer for retrieval).

Of the 72 spotted TMA ovarian cancer cases just one sample was positive with the IBL antibody. In contrast 14/72 samples were tested positive for CLDN6 when stained with the 58-4B antibody.

Unfortunately the quality of the commercial Ovarian Cancer TMA samples was low, resulting in weak staining signals on positive tumour samples. Therefore the comparison was repeated with tumour resection specimens from Dr. Dhaene, representing larger tumour regions with a high quality conservation of lung, uterine and testicular tumour samples.

The 58-4B staining resulted in a more sensitive and specific detection of CLDN6 in tumour samples compared to the stainings performed with the polyclonal IBL antibody, meaning more tumour cells were positive and a stronger intensity of the stained tumour cells was detected.

Example 9: Sequence Analysis of the Lead Antibodies

An analysis of the sequence of the antibodies 58-1B, 58-3A and 58-4B is shown in FIG. 5 and below.

| Amino acid sequence analysis of 58-4B-2 lead antibody | |
|---|---|
| Heavy chain (SEQ ID NO: 40) | EVQLQQSGTVLARPGASVRMSCRTSGYIFTTYWIHWVKER<br>PGQGLVWIGAIFPGNSDTTYNQKFRGKASLTAVTSASTAY<br>LDLSSLTDEDSAVYYCTREFYATWGQGTTLTVSS |
| Light chain (SEQ ID NO: 41) | DIVLTQNPLTLSVTIGQTASISCKSSQNLLYSDGKTYLNW<br>LLQRPGQSPKRLIYLMSKLDSGVPDRFTGSGSGTDFTLKI<br>SRVEAEDLGVYYCWQGTHFPWTFGGGTKLENT |

| Amino acid sequence analysis of 58-1B antibody | |
|---|---|
| Heavy chain (SEQ ID NO: 42) | EVQLQQSGTVLARPGASVKMSCRTSGYTFTTYWMHWVRERPGQGLEWIGAIYPENSDATYNQKFKGKASLTAVTSASTAYLELSSLTDEDSAVYYCTREFYATWGQGTTLTVSS |
| Light chain (SEQ ID NO: 43) | DVVMTQNPLTLSVTIGQTASISCKSSQNLLYSDGKTYLNWLLQRPGQSPKRLIYLMSKLDSGVPDRFTGSGSRTDFTLKISRVEAEDLGVYYCWQGTHFPWTFGGGTKLEIT |

| Amino acid sequence analysis of 58-3A antibody | |
|---|---|
| Heavy chain (SEQ ID NO: 44) | EVQLQQSGTVLARPGASVKMSCRTSGYTFTTYWMHWVRERPGQGLEWIGAIYPENSDATYNQKFKGKASLTAVTSASTAYLELSSLTDEDSAVYYCTREFYATWGQGTTLTVSS |
| Light chain (SEQ ID NO: 45) | DIVLTQNPLTLSVTIGQTASISCKSSQNLLYSDGKTYLNWLLQRPGQSPKRLIYLMSKLESGVPDRFTGSGSGTEFTLKISRVEAEDLGVYYCWQGTHFPWTFGGGTKLEIS |

TABLE 1

Overview Immunogens

| Immunogen | Konjugate-tag | Claudin6 Seq pos | Sequence | SEQ ID NO |
|---|---|---|---|---|
| Peptide 1 | KLH | AA 157-172 | CRDFYNPLVAEAQKREL | 46 |
| Peptide 2 | KLH | AA177-196 | GGGLLCCTCPSGGSQGPSHY | 47 |
| Peptide 3 | KLH | AA198-217 | CARYSTSAPAISRGPSEYPTK | 48 |
| Plasmid #5444 | His | AA182-220 | CCTCPSGGSQGPSHYMARYSTSAPAISRGPSEYPTKNYV+His-tag | 49 |
| Plasmid #5445 | GST | AA182-220 | CCTCPSGGSQGPSHYMARYSTSAPAISRGPSEYPTKNYV+GST-tag | 49 |
| Plasmid #448 | His | AA102-162 | AKCTTCVEEKDSKARLVLTSGIVFVISGVLTLIPVCWTAHAIIRDFYNPLVAEAQKRELGA+His | 50 |

TABLE 2

Immunization protocols for generation of antibodies

| Immunogen | Adjuvants | Immun. route | mAbs ELISA pos | mAB WB pos |
|---|---|---|---|---|
| Peptide1-KLH | Montanide | i.p. | 0 | 0 |
| Peptide1-KLH | CpG-PTO | i.m. | 1 | 1 |
| Peptide2-KLH | Montanide | i.p. | 0 | 0 |
| Peptide2-KLH | CpG-PTO | i.m. | 0 | 0 |
| Peptide3-KLH | Montanide | i.p. | 0 | 0 |
| Peptide3-KLH | CpG-PTO | i.m. | 0 | 0 |
| CLDN6_AA182-220_His | Gerbu | i.p. | 9 | 1 |
| CLDN6_AA182-220_GST | Gerbu | i.p. | 36 | 24 |
| CLDN6_AA102-121_His | Gerbu | i.p. | no fusion | |
| CLDN6_AA145-162_His | Gerbu | i.p. | no fusion | |

TABLE 2-continued

Immunization protocols for generation of antibodies

| Immunogen | Adjuvants | Immun. route | mAbs ELISA pos | mAB WB pos |
|---|---|---|---|---|
| CLDN6_AA102-162_His | Gerbu | i.p. | 32 | 0 |
| CLDN6_AA102-162_GST | Gerbu | i.p. | no fusion | |
| CLDN6_AA102-162_His | Montanide | i.p. | No fusion | |
| CLDN6_AA182-220_GST | Montanide | i.p. | 4 | 2 |
| CLDN6_AA182-220_His | Montanide | i.p. | 0 | 0 |
| CLDN6_AA182-220_His | IFA | s.c. | No fusion | |
| CLDN6_AA182-220_GST | IFA | s.c. | 6 | 5 |
| CLDN6_AA102-162_His | IFA | s.c. | No fusion | |

TABLE 3

Immunization schemes for lead antibodies
Mouse 569 Immunization #10-Fusion 58

| | | | | Mouse | Antigen | | Adjuvant | | Administration | |
|---|---|---|---|---|---|---|---|---|---|---|
| Date | Day | Event | Strain | ID | [μg] | Code | [μg] | Code | Route | Volume |
| 4 Jul. 2013 | 0 | 1. Immunization | C57BL/6 | 569 | 100 | C-terminal CLDN6-GST | 100 | Gerbu MM | i.p. | 200 μl |
| 15 Jul. 2013 | 11 | 2. Immunization | C57BL/6 | 569 | 50 | C-terminal CLDN6-GST | 100 | Gerbu MM | i.p. | 200 μl |
| 22 Jul. 2013 | 18 | 3. Immunization | C57BL/6 | 569 | 50 | C-terminal CLDN6-GST | 100 | Gerbu MM | i.p. | 200 μl |
| 29 Jul. 2013 | 25 | 4. Immunization | C57BL/6 | 569 | 50 | C-terminal CLDN6-GST | 100 | Gerbu MM | i.p. | 200 μl |
| 7 Aug. 2013 | 34 | 5. Immunization | C57BL/6 | 569 | 50 | C-terminal CLDN6-GST | 50 | Gerbu MM | i.p. | 200 μl |
| 14 Aug. 2013 | 41 | 6. Immunization | C57BL/6 | 569 | 50 | C-terminal CLDN6-GST | 50 | Gerbu MM | i.p. | 200 μl |
| 19 Aug. 2013 | 46 | 7. Immunization | C57BL/6 | 569 | 10 | C-terminal CLDN6-GST | 50 | Gerbu MM | i.p. | 200 μl |
| 26 Aug. 2013 | 53 | 8. Immunization | C57BL/6 | 569 | 10 | C-terminal CLDN6-GST | 50 | Gerbu MM | i.p. | 200 μl |
| 2 Sep. 2013 | 60 | 9. Immunization | C57BL/6 | 569 | 10 | C-terminal CLDN6-GST | 50 | Gerbu MM | i.p. | 200 μl |
| 30 Sep. 2013 | 88 | 10. Immunization | C57BL/6 | 569 | 10 | C-terminal CLDN6-GST | 50 | Gerbu MM | i.p. | 200 μl |
| 14 Oct. 2013 | 102 | 11. Immunization | C57BL/6 | 569 | 10 | C-terminal CLDN6-GST | 50 | Gerbu MM | i.p. | 200 μl |
| 4 Nov. 2013 | 123 | Boost | C57BL/6 | 569 | 100 | C-terminal CLDN6-His | | | i.p. | 200 μl |
| 7 Nov. 2013 | 126 | Fusion #58 | C57BL/6 | 569 | | | | | | |

TABLE 4

Two lots tested on normal tissue panel

| tissue | CLDN6 58-4B 5.0 μg/ml X00838 Lot. 100114 | CLDN6 58-4B 5.0 μg/ml X00856 Lot. 140407 |
|---|---|---|
| Adrenal Gland | 2/3 | 2/3 |
| Urinary Bladder | 0/2 | 0/1 |
| Eye | 1/2 | 1/2 |
| Breast | 0/2 | 0/2 |
| Brain, cerebellum | 1/3 | 1/3 |
| Brain, cerebral cortex | 0/3 | 0/3 |
| Fallopian Tube | 0/3 | 0/3 |
| Esophagus | 0/3 | 0/3 |
| Stomach | 0/3 | 0/3 |
| Small intestine | 1/3 | 0/2 |
| Colon | 2/3 | 2/3 |
| Rectum | 0/2 | 0/1 |
| Heart | 2/3 | 2/3 |
| Kidney | 4/6 | 2/6 |
| Liver | 3/3 | 3/3 |
| Lung | 0/3 | 0/3 |
| Ovary | 1/3 | 0/3 |
| Pancreas | 0/3 | 0/3 |
| Parathyroid | 0/1 | 0/1 |
| Pituitary | 2/2 | 0/2 |
| Placenta | 1/3 | 2/3 |
| Prostate | 0/3 | 0/3 |
| Skin | 0/2 | 0/2 |
| Spinal Cord. | 0/2 | 0/2 |
| Spleen | 1/2 | 0/2 |
| Muscle | 2/5 | 1/4 |
| Testis | 3/3 | 3/3 |
| Thymus | 0/3 | 0/3 |
| Thyroid | 1/3 | 0/3 |
| Tonsil | 1/3 | 0/3 |
| Ureter | 1/3 | 0/3 |
| Cervix | 0/3 | 0/3 |
| Uterus | 0/3 | 0/3 |

Identification of deposit for Accession Number DSM ACC3311 (Mouse (*Mus musculus*) myeloma Ag8.653 fused with mouse (*Mus musculus*) splenocytes; Hybridoma secreting antibody against human CLDN6) is shown in FIG. 7.

Identification of Further Deposits:

1) The Name and Address of Depositary Institution for the Deposits are:

Leibniz-Institut DSMZ-Deutsche Sammlung von Mikroorganismen und Zellkulturen GmbH Inhoffenstr. 7 B 38124 Braunschweig

DE

| Date of desposit | Accession Number | The indications made below relate to the deposited microorganism in the description on the following page(s) |
|---|---|---|
| Nov. 29, 2016 | DSM ACC3312 | page 4, line 29 |
| Nov. 29, 2016 | DSM ACC3313 | page 4, line 30 |

Additional Indications for all Above Mentioned Deposits:

Mouse (*Mus musculus*) myeloma Ag8.653 fused with mouse (*Mus musculus*) splenocytes Hybridoma secreting antibody against human CLDN6

2) Depositor:

All above mentioned depositions were made by:

Ganymed Pharmaceuticals AG

An der Goldgrube 12

55131 Mainz

DE

SEQUENCE LISTING

```
Sequence total quantity: 61
SEQ ID NO: 1           moltype = AA  length = 220
FEATURE                Location/Qualifiers
source                 1..220
                       mol_type = protein
                       organism = Homo sapiens
SEQUENCE: 1
```

```
MASAGMQILG VVLTLLGWVN GLVSCALPMW KVTAFIGNSI VVAQVVWEGL WMSCVVQSTG  60
QMQCKVYDSL LALPQDLQAA RALCVIALLV ALFGLLVYLA GAKCTTCVEE KDSKARLVLT  120
SGIVFVISGV LTLIPVCWTA HAIIRDFYNP LVAEAQKREL GASLYLGWAA SGLLLLGGGL  180
LCCTCPSGGS QGPSHYMARY STSAPAISRG PSEYPTKNYV                       220

SEQ ID NO: 2           moltype = AA  length = 217
FEATURE                Location/Qualifiers
source                 1..217
                       mol_type = protein
                       organism = Homo sapiens
SEQUENCE: 2
MASTGLELLG MTLAVLGWLG TLVSCALPLW KVTAFIGNSI VVAQVVWEGL WMSCVVQSTG  60
QMQCKVYDSL LALPQDLQAA RALCVIALLL ALLGLLVAIT GAQCTTCVED EGAKARIVLT  120
AGVILLLAGI LVLIPVCWTA HAIIQDFYNP LVAEALKREL GASLYLGWAA AALLMLGGGL  180
LCCTCPPPQV ERPRGPRLGY SIPSRSGASG LDKRDYV                          217

SEQ ID NO: 3           moltype = AA  length = 220
FEATURE                Location/Qualifiers
source                 1..220
                       mol_type = protein
                       organism = Homo sapiens
SEQUENCE: 3
MSMGLEITGT ALAVLGWLGT IVCCALPMWR VSAFIGSNII TSQNIWEGLW MNCVVQSTGQ  60
MQCKVYDSLL ALPQDLQAAR ALIVVAILLA AFGLLVALVG AQCTNCVQDD TAKAKITIVA  120
GVLFLLAALL TLVPVSWSAN TIIRDFYNPV VPEAQKREMG AGLYVGWAAA ALQLLGGALL  180
CCSCPPREKK YTATKVVYSA PRSTGPGASL GTGYDRKDYV                       220

SEQ ID NO: 4           moltype = AA  length = 209
FEATURE                Location/Qualifiers
source                 1..209
                       mol_type = protein
                       organism = Homo sapiens
SEQUENCE: 4
MASMGLQVMG IALAVLGWLA VMLCCALPMW RVTAFIGSNI VTSQTIWEGL WMNCVVQSTG  60
QMQCKVYDSL LALPQDLQAA RALVIISIIV AALGVLLSVV GGKCTNCLED ESAKAKTMIV  120
AGVVFLLAGL MVIVPVSWTA HNIIQDFYNP LVASGQKREM GASLYVGWAA SGLLLLGGGL  180
LCCNCPPRTD KPYSAKYSAA RSAAASNYV                                   209

SEQ ID NO: 5           moltype = AA  length = 219
FEATURE                Location/Qualifiers
source                 1..219
                       mol_type = protein
                       organism = Mus musculus
SEQUENCE: 5
MASTGLQILG IVLTLLGWVN ALVSCALPMW KVTAFIGNSI VVAQMVWEGL WMSCVVQSTG  60
QMQCKVYDSL LALPQDLQAA RALCVVTLLI VLLGLLVYLA GAKCTTCVED RNSKSRLVLI  120
SGIIFVISGV LTLIPVCWTA HSIIQDFYNP LVADAQKREL GASLYLGWAA SGLLLLGGGL  180
LCCACSSGGT QGPRHYMACY STSVPHSRGP SEYPTKNYV                        219

SEQ ID NO: 6           moltype = AA  length = 41
FEATURE                Location/Qualifiers
REGION                 1..41
                       note = Peptide
source                 1..41
                       mol_type = protein
                       organism = synthetic construct
SEQUENCE: 6
LLCCTCPSGG SQGPSHYMAR YSTSAPAISR GPSEYPTKNY V                     41

SEQ ID NO: 7           moltype = AA  length = 40
FEATURE                Location/Qualifiers
REGION                 1..40
                       note = Peptide
source                 1..40
                       mol_type = protein
                       organism = synthetic construct
SEQUENCE: 7
LLCCACSSGG TQGPRHYMAC YSTSVPHSRG PSEYPTKNYV                       40

SEQ ID NO: 8           moltype = AA  length = 38
FEATURE                Location/Qualifiers
REGION                 1..38
                       note = Peptide
source                 1..38
                       mol_type = protein
                       organism = synthetic construct
SEQUENCE: 8
CTCPSGGSQG PSHYMARYST SAPAISRGPS EYPTKNYV                         38
```

```
SEQ ID NO: 9            moltype = AA  length = 14
FEATURE                 Location/Qualifiers
REGION                  1..14
                        note = Peptide
source                  1..14
                        mol_type = protein
                        organism = synthetic construct
SEQUENCE: 9
CTCPSGGSQG PSHY                                                   14

SEQ ID NO: 10           moltype = AA  length = 15
FEATURE                 Location/Qualifiers
REGION                  1..15
                        note = Peptide
source                  1..15
                        mol_type = protein
                        organism = synthetic construct
SEQUENCE: 10
PSGGSQGPSH YMARY                                                  15

SEQ ID NO: 11           moltype = AA  length = 15
FEATURE                 Location/Qualifiers
REGION                  1..15
                        note = Peptide
source                  1..15
                        mol_type = protein
                        organism = synthetic construct
SEQUENCE: 11
SQGPSHYMAR YSTSA                                                  15

SEQ ID NO: 12           moltype = AA  length = 15
FEATURE                 Location/Qualifiers
REGION                  1..15
                        note = Peptide
source                  1..15
                        mol_type = protein
                        organism = synthetic construct
SEQUENCE: 12
SHYMARYSTS APAIS                                                  15

SEQ ID NO: 13           moltype = AA  length = 15
FEATURE                 Location/Qualifiers
REGION                  1..15
                        note = Peptide
source                  1..15
                        mol_type = protein
                        organism = synthetic construct
SEQUENCE: 13
ARYSTSAPAI SRGPS                                                  15

SEQ ID NO: 14           moltype = AA  length = 15
FEATURE                 Location/Qualifiers
REGION                  1..15
                        note = Peptide
source                  1..15
                        mol_type = protein
                        organism = synthetic construct
SEQUENCE: 14
TSAPAISRGP SEYPT                                                  15

SEQ ID NO: 15           moltype = AA  length = 15
FEATURE                 Location/Qualifiers
REGION                  1..15
                        note = Peptide
source                  1..15
                        mol_type = protein
                        organism = synthetic construct
SEQUENCE: 15
AISRGPSEYP TKNYV                                                  15

SEQ ID NO: 16           moltype = AA  length = 15
FEATURE                 Location/Qualifiers
REGION                  1..15
                        note = Peptide
source                  1..15
                        mol_type = protein
                        organism = synthetic construct
SEQUENCE: 16
YMARYSTSAP AISRG                                                  15
```

```
SEQ ID NO: 17          moltype = AA  length = 15
FEATURE                Location/Qualifiers
REGION                 1..15
                       note = Peptide
source                 1..15
                       mol_type = protein
                       organism = synthetic construct
SEQUENCE: 17
RYSTSAPAIS RGPSE                                                    15

SEQ ID NO: 18          moltype = AA  length = 15
FEATURE                Location/Qualifiers
REGION                 1..15
                       note = Peptide
source                 1..15
                       mol_type = protein
                       organism = synthetic construct
SEQUENCE: 18
YSTSAPAISR GPSEY                                                    15

SEQ ID NO: 19          moltype = AA  length = 15
FEATURE                Location/Qualifiers
REGION                 1..15
                       note = Peptide
source                 1..15
                       mol_type = protein
                       organism = synthetic construct
SEQUENCE: 19
STSAPAISRG PSEYP                                                    15

SEQ ID NO: 20          moltype = AA  length = 15
FEATURE                Location/Qualifiers
REGION                 1..15
                       note = Peptide
source                 1..15
                       mol_type = protein
                       organism = synthetic construct
SEQUENCE: 20
SAPAISRGPS EYPTK                                                    15

SEQ ID NO: 21          moltype = AA  length = 15
FEATURE                Location/Qualifiers
REGION                 1..15
                       note = Peptide
source                 1..15
                       mol_type = protein
                       organism = synthetic construct
SEQUENCE: 21
APAISRGPSE YPTKN                                                    15

SEQ ID NO: 22          moltype = AA  length = 15
FEATURE                Location/Qualifiers
REGION                 1..15
                       note = Peptide
source                 1..15
                       mol_type = protein
                       organism = synthetic construct
SEQUENCE: 22
PAISRGPSEY PTKNY                                                    15

SEQ ID NO: 23          moltype = AA  length = 14
FEATURE                Location/Qualifiers
REGION                 1..14
                       note = Peptide
source                 1..14
                       mol_type = protein
                       organism = synthetic construct
SEQUENCE: 23
ISRGPSEYPT KNYV                                                     14

SEQ ID NO: 24          moltype = AA  length = 13
FEATURE                Location/Qualifiers
REGION                 1..13
                       note = Peptide
source                 1..13
                       mol_type = protein
                       organism = synthetic construct
SEQUENCE: 24
```

-continued

```
SRGPSEYPTK NYV                                                    13

SEQ ID NO: 25           moltype = AA  length = 12
FEATURE                 Location/Qualifiers
REGION                  1..12
                        note = Peptide
source                  1..12
                        mol_type = protein
                        organism = synthetic construct
SEQUENCE: 25
RGPSEYPTKN YV                                                     12

SEQ ID NO: 26           moltype = AA  length = 11
FEATURE                 Location/Qualifiers
REGION                  1..11
                        note = Peptide
source                  1..11
                        mol_type = protein
                        organism = synthetic construct
SEQUENCE: 26
GPSEYPTKNY V                                                      11

SEQ ID NO: 27           moltype = AA  length = 10
FEATURE                 Location/Qualifiers
REGION                  1..10
                        note = Peptide
source                  1..10
                        mol_type = protein
                        organism = synthetic construct
SEQUENCE: 27
PSEYPTKNYV                                                        10

SEQ ID NO: 28           moltype = AA  length = 9
FEATURE                 Location/Qualifiers
REGION                  1..9
                        note = Peptide
source                  1..9
                        mol_type = protein
                        organism = synthetic construct
SEQUENCE: 28
SEYPTKNYV                                                         9

SEQ ID NO: 29           moltype = AA  length = 8
FEATURE                 Location/Qualifiers
REGION                  1..8
                        note = Peptide
source                  1..8
                        mol_type = protein
                        organism = synthetic construct
SEQUENCE: 29
EYPTKNYV                                                          8

SEQ ID NO: 30           moltype = AA  length = 7
FEATURE                 Location/Qualifiers
REGION                  1..7
                        note = Peptide
source                  1..7
                        mol_type = protein
                        organism = synthetic construct
SEQUENCE: 30
YPTKNYV                                                           7

SEQ ID NO: 31           moltype = AA  length = 6
FEATURE                 Location/Qualifiers
REGION                  1..6
                        note = Peptide
source                  1..6
                        mol_type = protein
                        organism = synthetic construct
SEQUENCE: 31
PTKNYV                                                            6

SEQ ID NO: 32           moltype = AA  length = 5
FEATURE                 Location/Qualifiers
REGION                  1..5
                        note = Peptide
source                  1..5
                        mol_type = protein
                        organism = synthetic construct
```

```
SEQUENCE: 32
PTKNY                                                           5

SEQ ID NO: 33          moltype = AA  length = 4
FEATURE                Location/Qualifiers
REGION                 1..4
                       note = Peptide
source                 1..4
                       mol_type = protein
                       organism = synthetic construct
SEQUENCE: 33
PTKN                                                            4

SEQ ID NO: 34          moltype = AA  length = 40
FEATURE                Location/Qualifiers
REGION                 1..40
                       note = Peptide
source                 1..40
                       mol_type = protein
                       organism = synthetic construct
SEQUENCE: 34
LCCTCPSGGS QGPSHYMARY STSAPAISRG PSEYPTKNYV                     40

SEQ ID NO: 35          moltype = AA  length = 37
FEATURE                Location/Qualifiers
REGION                 1..37
                       note = Peptide
source                 1..37
                       mol_type = protein
                       organism = synthetic construct
SEQUENCE: 35
LCCTCPPPQV ERPRGPRLGY SIPSRSGASG LDKRDYV                        37

SEQ ID NO: 36          moltype = AA  length = 41
FEATURE                Location/Qualifiers
REGION                 1..41
                       note = Peptide
source                 1..41
                       mol_type = protein
                       organism = synthetic construct
SEQUENCE: 36
LCCSCPPREK KYTATKVVYS APRSTGPGAS LGTGYDRKDY V                   41

SEQ ID NO: 37          moltype = AA  length = 29
FEATURE                Location/Qualifiers
REGION                 1..29
                       note = Peptide
source                 1..29
                       mol_type = protein
                       organism = synthetic construct
SEQUENCE: 37
LCCNCPPRTD KPYSAKYSAA RSAAASNYV                                 29

SEQ ID NO: 38          moltype = AA  length = 7
FEATURE                Location/Qualifiers
REGION                 1..7
                       note = Peptide
source                 1..7
                       mol_type = protein
                       organism = synthetic construct
SEQUENCE: 38
EYPTKNY                                                         7

SEQ ID NO: 39          moltype = AA  length = 4
FEATURE                Location/Qualifiers
REGION                 1..4
                       note = Peptide
source                 1..4
                       mol_type = protein
                       organism = synthetic construct
SEQUENCE: 39
RGPS                                                            4

SEQ ID NO: 40          moltype = AA  length = 114
FEATURE                Location/Qualifiers
REGION                 1..114
                       note = Antibody chain
source                 1..114
                       mol_type = protein
```

```
                         organism = synthetic construct
SEQUENCE: 40
EVQLQQSGTV LARPGASVRM SCRTSGYIFT TYWIHWVKER PGQGLVWIGA IFPGNSDTTY  60
NQKFRGKASL TAVTSASTAY LDLSSLTDED SAVYYCTREF YATWGQGTTL TVSS        114

SEQ ID NO: 41            moltype = AA  length = 112
FEATURE                  Location/Qualifiers
REGION                   1..112
                         note = Antibody chain
source                   1..112
                         mol_type = protein
                         organism = synthetic construct
SEQUENCE: 41
DIVLTQNPLT LSVTIGQTAS ISCKSSQNLL YSDGKTYLNW LLQRPGQSPK RLIYLMSKLD  60
SGVPDRFTGS GSGTDFTLKI SRVEAEDLGV YYCWQGTHFP WTFGGGTKLE NT          112

SEQ ID NO: 42            moltype = AA  length = 114
FEATURE                  Location/Qualifiers
REGION                   1..114
                         note = Antibody chain
source                   1..114
                         mol_type = protein
                         organism = synthetic construct
SEQUENCE: 42
EVQLQQSGTV LARPGASVKM SCRTSGYTFT TYWMHWVRER PGQGLEWIGA IYPENSDATY  60
NQKFKGKASL TAVTSASTAY LELSSLTDED SAVYYCTREF YATWGQGTTL TVSS        114

SEQ ID NO: 43            moltype = AA  length = 112
FEATURE                  Location/Qualifiers
REGION                   1..112
                         note = Antibody chain
source                   1..112
                         mol_type = protein
                         organism = synthetic construct
SEQUENCE: 43
DVVMTQNPLT LSVTIGQTAS ISCKSSQNLL YSDGKTYLNW LLQRPGQSPK RLIYLMSKLD  60
SGVPDRFTGS GSRTDFTLKI SRVEAEDLGV YYCWQGTHFP WTFGGGTKLE IT          112

SEQ ID NO: 44            moltype = AA  length = 114
FEATURE                  Location/Qualifiers
REGION                   1..114
                         note = Antibody chain
source                   1..114
                         mol_type = protein
                         organism = synthetic construct
SEQUENCE: 44
EVQLQQSGTV LARPGASVKM SCRTSGYTFT TYWMHWVRER PGQGLEWIGA IYPENSDATY  60
NQKFKGKASL TAVTSASTAY LELSSLTDED SAVYYCTREF YATWGQGTTL TVSS        114

SEQ ID NO: 45            moltype = AA  length = 112
FEATURE                  Location/Qualifiers
REGION                   1..112
                         note = Antibody chain
source                   1..112
                         mol_type = protein
                         organism = synthetic construct
SEQUENCE: 45
DIVLTQNPLT LSVTIGQTAS ISCKSSQNLL YSDGKTYLNW LLQRPGQSPK RLIYLMSKLE  60
SGVPDRFTGS GSGTEFTLKI SRVEAEDLGV YYCWQGTHFP WTFGGGTKLE IS          112

SEQ ID NO: 46            moltype = AA  length = 17
FEATURE                  Location/Qualifiers
REGION                   1..17
                         note = Peptide
source                   1..17
                         mol_type = protein
                         organism = synthetic construct
SEQUENCE: 46
CRDFYNPLVA EAQKREL                                                 17

SEQ ID NO: 47            moltype = AA  length = 20
FEATURE                  Location/Qualifiers
REGION                   1..20
                         note = Peptide
source                   1..20
                         mol_type = protein
                         organism = synthetic construct
SEQUENCE: 47
GGGLLCCTCP SGGSQGPSHY                                              20
```

```
SEQ ID NO: 48          moltype = AA  length = 21
FEATURE                Location/Qualifiers
REGION                 1..21
                       note = Peptide
source                 1..21
                       mol_type = protein
                       organism = synthetic construct
SEQUENCE: 48
CARYSTSAPA ISRGPSEYPT K                                            21

SEQ ID NO: 49          moltype = AA  length = 39
FEATURE                Location/Qualifiers
REGION                 1..39
                       note = Peptide
source                 1..39
                       mol_type = protein
                       organism = synthetic construct
SEQUENCE: 49
CCTCPSGGSQ GPSHYMARYS TSAPAISRGP SEYPTKNYV                         39

SEQ ID NO: 50          moltype = AA  length = 61
FEATURE                Location/Qualifiers
REGION                 1..61
                       note = Peptide
source                 1..61
                       mol_type = protein
                       organism = synthetic construct
SEQUENCE: 50
AKCTTCVEEK DSKARLVLTS GIVFVISGVL TLIPVCWTAH AIIRDFYNPL VAEAQKRELG  60
A                                                                  61

SEQ ID NO: 51          moltype = AA  length = 8
FEATURE                Location/Qualifiers
REGION                 1..8
                       note = Variable heavy chain CDR
source                 1..8
                       mol_type = protein
                       organism = synthetic construct
SEQUENCE: 51
GYIFTTYW                                                           8

SEQ ID NO: 52          moltype = AA  length = 8
FEATURE                Location/Qualifiers
REGION                 1..8
                       note = Variable heavy chain CDR
source                 1..8
                       mol_type = protein
                       organism = synthetic construct
SEQUENCE: 52
IFPGNSDT                                                           8

SEQ ID NO: 53          moltype = AA  length = 7
FEATURE                Location/Qualifiers
REGION                 1..7
                       note = Variable heavy chain CDR
source                 1..7
                       mol_type = protein
                       organism = synthetic construct
SEQUENCE: 53
TREFYAT                                                            7

SEQ ID NO: 54          moltype = AA  length = 11
FEATURE                Location/Qualifiers
REGION                 1..11
                       note = Variable light chain CDR
source                 1..11
                       mol_type = protein
                       organism = synthetic construct
SEQUENCE: 54
QNLLYSDGKT Y                                                       11

SEQ ID NO: 55          moltype =   length =
SEQUENCE: 55
000

SEQ ID NO: 56          moltype = AA  length = 9
FEATURE                Location/Qualifiers
REGION                 1..9
```

-continued

```
                         note = Variable light chain CDR
source                   1..9
                         mol_type = protein
                         organism = synthetic construct
SEQUENCE: 56
WQGTHFPWT                                                  9

SEQ ID NO: 57            moltype = AA  length = 8
FEATURE                  Location/Qualifiers
REGION                   1..8
                         note = Variable heavy chain CDR
source                   1..8
                         mol_type = protein
                         organism = synthetic construct
SEQUENCE: 57
GYTFTTYW                                                   8

SEQ ID NO: 58            moltype = AA  length = 8
FEATURE                  Location/Qualifiers
REGION                   1..8
                         note = Variable heavy chain CDR
source                   1..8
                         mol_type = protein
                         organism = synthetic construct
SEQUENCE: 58
IYPENSDA                                                   8

SEQ ID NO: 59            moltype = AA  length = 5
FEATURE                  Location/Qualifiers
REGION                   1..5
                         note = Peptide
source                   1..5
                         mol_type = protein
                         organism = synthetic construct
SEQUENCE: 59
EYPTK                                                      5

SEQ ID NO: 60            moltype = AA  length = 6
FEATURE                  Location/Qualifiers
REGION                   1..6
                         note = Peptide
source                   1..6
                         mol_type = protein
                         organism = synthetic construct
SEQUENCE: 60
EYPTKN                                                     6

SEQ ID NO: 61            moltype = AA  length = 6
FEATURE                  Location/Qualifiers
REGION                   1..6
                         note = Peptide
source                   1..6
                         mol_type = protein
                         organism = synthetic construct
SEQUENCE: 61
YPTKNY                                                     6
```

We claim:

1. An antibody that binds to claudin 6 (CLDN6), wherein said antibody comprises:

(a) an antibody heavy chain variable region (VH) comprising the amino acid sequence set forth in SEQ ID NO: 40 and an antibody light chain variable region (VL) comprising the amino acid sequence set forth in SEQ ID NO: 41;

(b) an antibody heavy chain variable region (VH) comprising the amino acid sequence set forth in SEQ ID NO: 42 and an antibody light chain variable region (VL) comprising the amino acid sequence set forth in SEQ ID NO: 43; or (c) an antibody heavy chain variable region (VH) comprising the amino acid sequence set forth in SEQ ID NO: 44 and an antibody light chain variable region (VL) comprising the amino acid sequence set forth in SEQ ID NO: 45.

2. A diagnostic test kit comprising the antibody of claim 1 and at least one detectable label.

3. The diagnostic test kit of claim 2, wherein the detectable label is an indicator enzyme, a radiolabel, a fluorophore, or a paramagnetic particle.

4. The diagnostic test kit of claim 2, wherein the VH has the amino acid sequence set forth in SEQ ID NO: 40 and the VL has the amino acid sequence set forth in SEQ ID NO: 41.

5. The diagnostic test kit of claim 2, wherein the VH has the amino acid sequence set forth in SEQ ID NO: 42 and the VL has the amino acid sequence set forth in SEQ ID NO: 43.

6. The diagnostic test kit of claim 2, wherein the VH has the amino acid sequence set forth in SEQ ID NO: 44 and the VL has the amino acid sequence set forth in SEQ ID NO: 45.

7. A conjugate comprising the antibody of claim 1 coupled to at least one label.

8. The conjugate of claim 7, wherein the label is a detectable label.

9. The conjugate of claim 7, wherein the label is a fluorescent label, a luminescent label, a chromophore label, a radioisotopic label, an isotopic label, an isobaric label, an enzyme label, a particle label, a small organic molecule, a ligand of a receptor or a binding molecule, a label-sequence comprising nucleic acids and/or amino acid residues which can be detected by use of binding agents.

10. A method for determining whether a cancer is treatable by a cancer therapy targeting CLDN6 or determining the prognosis of a patient having cancer comprising the steps of:

(i) contacting a sample comprising cancer cells with the antibody of claim 1 and (ii) detecting the formation of a complex or the quantity of a complex between the antibody or the antigen-binding fragment and CLDN6.

11. The method of claim 10, wherein the VH has the amino acid sequence set forth in SEQ ID NO: 40 and the VL has the amino acid sequence set forth in SEQ ID NO: 41.

12. The method of claim 10, wherein the VH has the amino acid sequence set forth in SEQ ID NO: 42 and the VL has the amino acid sequence set forth in SEQ ID NO: 43.

13. The method of claim 10, wherein the VH has the amino acid sequence set forth in SEQ ID NO: 44 and the VL has the amino acid sequence set forth in SEQ ID NO: 45.

14. One or more nucleic acids comprising:

(a) a nucleic acid sequence encoding an antibody heavy chain variable region (VH) comprising the amino acid sequence set forth in SEQ ID NO: 40 and a nucleic acid sequence encoding an antibody light chain variable region (VL) comprising the amino acid sequence set forth in SEQ ID NO: 41;

(b) a nucleic acid sequence encoding an antibody heavy chain variable region (VH) comprising the amino acid sequence set forth in SEQ ID NO: 42 and a nucleic acid sequence encoding an antibody light chain variable region (VL) comprising the amino acid sequence set forth in SEQ ID NO: 43; or (c) a nucleic acid sequence encoding an antibody heavy chain variable region (VH) comprising the amino acid sequence set forth in SEQ ID NO: 44 and a nucleic acid sequence encoding an antibody light chain variable region (VL) comprising the amino acid sequence set forth in SEQ ID NO: 45.

15. The one or more nucleic acids of claim 14, wherein at least one of said nucleic acid sequences is operatively linked to an expression control element.

16. The one or more nucleic acids of claim 15, wherein said expression control sequence allows expression in a prokaryotic or eukaryotic host cell.

17. A recombinant cell comprising the one or more nucleic acids of claim 14.

18. The recombinant cell of claim 17, wherein said recombinant cell is a CHO cell, an NS/0 cell, a HEK293 cell, a HEK293T cell, a plant cell, or a fungal cell.

* * * * *